United States Patent
Obropta, Jr. et al.

(10) Patent No.: US 10,555,697 B2
(45) Date of Patent: Feb. 11, 2020

(54) DIGITAL IMAGE CORRELATION FOR MEASURING SKIN STRAIN AND DEFORMATION

(71) Applicant: Massachusetts Institute of Technology, Cambridge, MA (US)

(72) Inventors: Edward W. Obropta, Jr., Cape May Court House, NJ (US); Dava J. Newman, Marblehead, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 427 days.

(21) Appl. No.: 15/514,297

(22) PCT Filed: Oct. 5, 2015

(86) PCT No.: PCT/US2015/053978
§ 371 (c)(1),
(2) Date: Mar. 24, 2017

(87) PCT Pub. No.: WO2016/076975
PCT Pub. Date: May 19, 2016

(65) Prior Publication Data
US 2017/0281009 A1    Oct. 5, 2017

Related U.S. Application Data

(63) Continuation-in-part of application No. 14/837,455, filed on Aug. 27, 2015, now Pat. No. 10,028,697,
(Continued)

(51) Int. Cl.
*A61B 5/00* (2006.01)
*A61B 5/11* (2006.01)
*A41H 1/00* (2006.01)

(52) U.S. Cl.
CPC ............... *A61B 5/442* (2013.01); *A41H 1/00* (2013.01); *A61B 5/0077* (2013.01);
(Continued)

(58) Field of Classification Search
CPC ..... A61B 5/442; A61B 5/1127; A61B 5/7225; A61B 5/0077; A61B 5/1121;
(Continued)

(56) References Cited

U.S. PATENT DOCUMENTS

| | | |
|---|---|---|
| 4,000,524 A | 1/1977 | Rinehart |
| 4,654,896 A | 4/1987 | Rinehart |

(Continued)

FOREIGN PATENT DOCUMENTS

| | | |
|---|---|---|
| WO | WO 93/22624 | 11/1993 |
| WO | WO 2009/100020 A4 | 8/2009 |

(Continued)

OTHER PUBLICATIONS

Bethke, et al.; "Bio-Suit Development: Viable Options for Mechanical Counter Pressure;" SAE Technical Paper Series; 34th International Conference on Environmental Systems (ICES); Jul. 19-22, 2004; 14 pages.
(Continued)

*Primary Examiner* — Sean P Dougherty
(74) *Attorney, Agent, or Firm* — Daly, Crowley, Mofford & Durkee, LLP

(57) ABSTRACT

Described embodiments provide a system and method for measuring surface deformation and strain using digital image correlation of a surface of a test object. A data acquisition system acquires images of the surface. The surface has a unique surface pattern to facilitate image acquisition. The images are grouped into one or more image sets. Three dimensional image correlation is performed on each of the image sets to determine deformation and strain
(Continued)

data. The deformation and strain data from the image sets are stitched into one dataset. Principal strains and lines of non-extension (LoNEs) directions are determined. One or more LoNEs streamlines and lines of maximum and minimum extensions are determined. Visualizations for the strain magnitudes, LoNE streamlines, maximum and minimum extension streamlines are generated in three dimensions.

25 Claims, 19 Drawing Sheets

Related U.S. Application Data which is a continuation of application No. 13/274,992, filed on Oct. 17, 2011, now Pat. No. 9,149,224.

(60) Provisional application No. 62/079,820, filed on Nov. 14, 2014.

(52) U.S. Cl.
CPC .......... *A61B 5/1121* (2013.01); *A61B 5/1127* (2013.01); *A61B 5/7225* (2013.01); *A61B 5/7278* (2013.01); *A61B 5/0064* (2013.01); *A61B 5/6828* (2013.01); *A61B 2562/0261* (2013.01); *A61B 2576/02* (2013.01)

(58) Field of Classification Search
CPC ........ A61B 2576/02; A61B 2562/0261; A61B 5/6828; A61B 5/0064
See application file for complete search history.

(56) References Cited

U.S. PATENT DOCUMENTS

| | | | |
|---|---|---|---|
| 4,969,106 | A | 11/1990 | Vogel et al. |
| 5,056,530 | A | 10/1991 | Butler et al. |
| 5,167,038 | A | 12/1992 | Rinehart |
| 5,641,955 | A | 6/1997 | Bonniau et al. |
| 5,757,473 | A | 5/1998 | Kanduth et al. |
| 6,345,191 | B1 | 2/2002 | Hartmann et al. |
| 6,389,200 | B1 | 5/2002 | Foltzer |
| 6,809,462 | B2 | 10/2004 | Pelrine et al. |
| 7,281,275 | B2 | 10/2007 | Bitzer |
| 9,149,224 | B1 | 10/2015 | Newman et al. |
| 2003/0013994 | A1 | 1/2003 | Rubinstenn et al. |
| 2003/0065278 | A1 | 4/2003 | Rubinstenn et al. |
| 2005/0264561 | A1 | 12/2005 | Anast et al. |
| 2006/0056661 | A1 | 3/2006 | Einighammer et al. |
| 2007/0167879 | A1 | 7/2007 | Cochran |
| 2007/0186642 | A1 | 8/2007 | Sano et al. |
| 2008/0234607 | A1 | 9/2008 | Hunter-Jones et al. |
| 2009/0255531 | A1 | 10/2009 | Johnson et al. |
| 2009/0315989 | A1 | 12/2009 | Adelson |
| 2010/0000547 | A1 | 1/2010 | Johnson et al. |
| 2011/0288447 | A1 | 11/2011 | Cochran |
| 2011/0319791 | A1 | 12/2011 | Harry et al. |
| 2012/0238914 | A1 | 9/2012 | Goldfield et al. |
| 2013/0116601 | A1 | 5/2013 | Tomazic et al. |
| 2014/0081187 | A1 | 3/2014 | Wyatt et al. |
| 2014/0277729 | A1* | 9/2014 | Nakamura ............ G01L 5/0076 700/258 |
| 2014/0277739 | A1 | 9/2014 | Kornbluh et al. |
| 2014/0311187 | A1* | 10/2014 | Amarasiriwardena . .................... A41B 11/00 66/178 R |
| 2015/0073318 | A1 | 3/2015 | Holschuh et al. |
| 2015/0073319 | A1 | 3/2015 | Holschuh et al. |
| 2016/0317079 | A1 | 11/2016 | Newman et al. |

FOREIGN PATENT DOCUMENTS

| | | |
|---|---|---|
| WO | WO 2011/109029 A1 | 9/2011 |
| WO | WO 2016/077150 A1 | 5/2016 |

OTHER PUBLICATIONS

Newman, et al.; "Astronaut Bio-Suit System to Enable Planetary Exploration;" 55'th International Astronautical Congress; 2004; pp. 1-22.
Newman, et al.; "Revolutionary Design for Astronaut Exploration—Beyond the Bio-Suit System;" vol. 880, Jan. 30, 2007; 12 pages.
Wolfrum, et al.; "An Automatic Procedure To Map the Skin Strain Field with Application To Advanced Locomotion Space Suit Design;" $5^{th}$ World Congress of Biomechanics, Munich, Jul. 29-Aug. 4, 2006; 2 pages.
Iberall; "The Use of Lines of Nonextension to Improve Mobility in Full-Pressure Suits;" Technical Report—AMRL-TR-64-118; Wright-Patterson Air Force Base; Nov. 1964; 44 pages.
Iberall; "Use of Lines of Nonextension to Provide Mobility in Full-Pressure Suits;" an ASME Publication; American Society of Mechanical Engineers; Nov. 16-20, 1969; 17 pages.
Domingues, et al.; "Skin Strain Field Analysis of the Human Ankle Joint;" $4^{th}$ Congress Nacional De Biomecanica; Feb. 4-5, 2010; 6 pages.
Marreiros; "Skin Strain Field Analysis of the Human Ankle Joint;" Dissertation; Instituto Superior Tecninco; Faculdade De Medicina; Nov. 2010; 73 pages.
Non-Final Office Action dated Aug. 1, 2014, for U.S. Appl. No. 13/274,992; 20 pages.
Response filed on Dec. 1, 2014 to Non-Final Office Action dated Aug. 1, 2014; for U.S. Appl. No. 13/274,992; 21 pages.
Final Office Action dated Jan. 28, 2015, for U.S. Appl. No. 13/274,992; 11 pages.
Response filed on May 28, 2015 to Final Office Action dated Jan. 28, 2015; for U.S. Appl. No. 13/274,992; 7 pages.
Supplemental Response filed on Jun. 1, 2015 to Final Office Action dated Jan. 28, 2015; for U.S. Appl. No. 13/274,992; 12 pages.
Notice of Allowance dated Jun. 11, 2015, for U.S. Appl. No. 13/274,992; 9 pages.
Bethke, Kristen "The second skin approach: skin strain field analysis and mechanical counter pressure prototyping for advanced spacesuit design"; with Abstract and Chapters 3, 4 and 5, pp. 41-114 (78 pages), 2005; Retrieved from the Internet. <URL:http://dspace.mit.edu/bitstream/handle/1721.1/32443/61719483-MIT.pdf?sequence=2>.
PCT Search Report and Written Opinion of the ISA, PCT/US2015/053978 dated Jan. 6, 2016; 8 pages.
Ross et al., Recovery Force_1; U.S. Appl. No. 61/701,329, filed Sep. 14, 2012; 18 pages.
Ambrosino, et al.; "Novel Magnetic Sensor Based on Fiber Bragg Grating and Magnetic Shape Memory Alloys;" $1^{st}$ International Conference on Sensing Technology; Nov. 21-23, 2005; 6 pages.
Holschuh, et al.; "Morphing Compression Garments for Space Medicine and Extravehicular Activity Using Active Materials;" Aerospace Medicine and Human Performance; vol. 87; No. 2; Feb. 2016; 9 pages.
Holschuh, et al.; "Two-Spring Model for Active Compression Textiles with Integrated NiTi Coil Actuators;" IOP Publishing; Smart Materials and Structures; Feb. 6, 2015; 14 pages.
Park, et al.; "Exoskeletal Force-Sensing End-Effectors With Embedded Optical Fiber-Bragg-Grating Sensors;" IEEE Transactions on Robotics; vol. 25; No. 6; Dec. 2009; 13 pages.
Stirling, et al.; Applicability of Shape Memory Alloy Wire for an Active, Soft Orthotic;: Journal of Materials Engineering and Performance; ASM International; Feb. 8, 2011; 5 pages.
Witt, et al.; "Medical Textiles with Embedded Fiber Optic Sensors for Monitoring of Respiratory Movement;" IEEE Sensors Journal; vol. 12; No. 1; Jan. 2012; 9 pages.
Notice of Allowance Dated May 16, 2018 for U.S. Appl. No. 14/837,455; 7 Pages.
Response to U.S. Non-Final Office Action dated Dec. 20, 2017 for U.S. Appl. No. 14/837,455; Response filed on Mar. 20, 2018; 12 pages.

(56) References Cited

OTHER PUBLICATIONS

PCT International Preliminary Report on Patentability dated May 26, 2017 from International Application No. PCT/US2015/053978; 7 Pages.

* cited by examiner

608

800

900

1012

DIGITAL IMAGE CORRELATION FOR MEASURING SKIN STRAIN AND DEFORMATION

CROSS-REFERENCE TO RELATED APPLICATIONS

This application is a U.S. National Stage of PCT application PCT/US2015/053978 filed in the English language on Oct. 5, 2015, and entitled "DIGITAL IMAGE CORRELATION FOR MEASURING SKIN STRAIN AND DEFORMATION ", which claims the benefit under 35 U.S.C. § 119of provisional application number 62/079,820 filed Nov. 14, 2014. This application is also a continuation-in-part, and claims the benefit under 35 U.S.C. § 120 of co-pending U.S. patent application Ser. No. 14/837,455 filed on Aug. 27, 2015, which is a continuation of U.S. patent application Ser. No. 13/274, 992 filed on Oct. 17, 2011, now U.S. Pat. No. 9,149,224 both of which application are hereby incorporated herein by reference in their entireties.

STATEMENT REGARDING FEDERALLY SPONSORED RESEARCH OR DEVELOPMENT

This invention was made with government support under Contract No. N00014-13-P-1193 awarded by the United States Office of Naval Research. The government has certain rights in the invention.

BACKGROUND

In order to experience outer space first hand, space suits are needed to protect astronauts from the extreme environment. The human body requires pressure to be continually and evenly applied. On Earth, the atmosphere applies 101.325 kPa (I atmosphere at sea-level) to the surface of the human body. In the vacuum of space, pressure must be applied using a pressurized capsule or space suit. The safe minimum pressure is limited by breathing pure oxygen at a pressure of 25.33 kPa, although this low pressure requires a long duration of time to transition from an atmosphere with inert gases to avoid decompression sickness. Ideal space suits would have a pressure of 101.325 kPa to have zero transition time, but this makes traditional space suits too stiff to move.

Current space suits limit astronaut mobility and cause fatigue. Arthur Iberall worked on ways to develop mobile pressurized space suits and developed the concept of the Lines of Non-extension (LoNEs) to describe the deformation and motion of human skin. LoNEs are contours along the human body where the skin does not stretch. Other approaches to make mobile space suits were developed, such as the Space Activity Suit, a mechanical counter pressure (MCP) space suit that used material elasticity to pressurize the body instead of gas pressure. In 2001, the concept of a fully MCP spacesuit reemerged at the Massachusetts Institute of Technology (MIT) as the Bio-Suit. The concepts of MCP have also been applied to different components of space suits, such as gloves.

Research on skin deformation and physiology dates back to the mid-1800s with Karl Langer's 1861 study of the direction in which the skin deforms when punctured. The directions and lines are now known as Langer Lines. Space suit and bio-medical research has progressed our understanding of skin's deformation characteristics. This body of research has developed various techniques to quantify skin strain using laser scanning and motion capture systems. However, in past research, measurements have been limited to 1 $cm^2$, which limits the ability to accurately compute LoNEs. Using past techniques, it was also difficult to analyze multiple subjects. Thus, there is need for new measurement techniques that improve upon prior techniques.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

One aspect provides a method for measuring surface deformation and strain using digital image correlation of a surface of a test object. A data acquisition system acquires images of the surface. The surface has a unique surface pattern to facilitate image acquisition. The images are grouped into one or more image sets. Three dimensional image correlation is performed on each of the image sets to determine deformation and strain data. The deformation and strain data from the image sets are stitched into one dataset. Principal strains and lines of non-extension (LoNEs) directions are determined. One or more LoNEs streamlines and lines of maximum and minimum extensions are determined. Visualizations for the strain magnitudes, LoNE streamlines, maximum and minimum extension streamlines are generated in three dimensions.

In an embodiment, a pattern for one or more customized coverings for the test object is generated based on one or more of the determined principal strains, lines of non-extension (LoNEs) directions, the one or more LoNEs streamlines and the lines of maximum and minimum extensions. In an embodiment, the surface is human skin and the test object is a human, and the one or more custom coverings comprise at least one of: custom garments, custom orthotics, custom prosthetics and custom wearable electronic devices. In an embodiment, the one or more customized coverings are generated based on the generated pattern. In an embodiment, the unique surface pattern is generated having a pattern with a granularity determined to provide image tracking resolution of approximately 1 $mm^2$ and is applied to the surface. In an embodiment, an application tool to apply the unique surface pattern to the surface is generated.

In an embodiment, stitching the data from the image sets into one dataset includes converting the image sets from into a plurality of meshes and stitching the meshes together at points of overlap between each mesh. In an embodiment, at a point of overlap between the meshes, the data of the image sets is merged by re-meshing the data at the overlap point. In an embodiment, at a point of overlap between the meshes, the data is merged by averaging data of the image sets at the overlap point. In an embodiment, at a point of overlap between the meshes, a measurement quality index, q, is determined, and data from the image sets that reach a predetermined threshold of q is kept, and data from the image sets that do not reach the predetermined threshold of q is discarded. In an embodiment, q is defined as an inverse of a standard deviation of a matching error of the image sets given by q=1/σ. In an embodiment, the image sets are in a curvilinear grid data format, and the meshes are triangular meshes.

In an embodiment, determining principal strains and lines of non-extension (LoNEs) directions includes identifying and determining motion of, based on the unique surface pattern, pixel groups from an image of an initial position of the surface and from an image of a deformed position of the surface. One or more strains of each pixel group are determined and projected onto a two-dimensional (2D) plane tangent to the surface. The projected strains are rotated onto axes defined with respect to the surface. A longitudinal strain, a circumferential strain, a shear strain and principal strains for each pixel group are generated based on the rotated strains. If the principal strains associated with each pixel group have opposite signs, an angle of a line of non-extension for the pixel group is determined based on the principal strains. If the principal strains associated with each pixel group have opposite signs, an angle of minimum extension or minimum compression for the pixel group is determined. The determined angle of a line of non-extension or angles of minimum extension or minimum compression for each pixel group is projected onto the body surface, and angles of lines of non-extension are connected into streamlines. In an embodiment, determining one or more strains surrounding each marker point includes calculating at least one of: Lagrangian strains and Euler-Almansi strains. In an embodiment, the 2D tangential plane is generated by averaging normal vectors to the planes between neighboring pairs of strain vectors associated with the corresponding pixel group. A neighboring pair of strain vectors includes strain vectors associated with pixel groups that are adjacent to one another.

In an embodiment, determining one or more LoNEs streamlines and determining lines of maximum and minimum extensions includes selecting one or more seed points within the image sets and linearly interpolating a vector filed of LoNEs directions of the image sets by transforming to a local tangential coordinate system. Streamlines are determined where a current position plus a velocity at that point multiplied by a time step equals a new position. The determined streamlines are translated from a 2D coordinate system to a 3D coordinate system.

In an embodiment, the image data is acquired by one or more stereoscopic camera pairs. In an embodiment, the image data is acquired by at least one of: one or more optical cameras, computed tomography (CT) and magnetic resonance imaging (MRI). In an embodiment, deformation data is acquired from one or more sensors in contact with the surface.

In another aspect, a system is provided for measuring surface deformation and strain using digital image correlation of a surface of a test object. The system includes a data collection system configured to acquire images of the surface, the surface having a unique surface pattern and a lines of non-extension (LoNEs) processor. The LoNEs processor is configured to group the images into one or more image sets and perform three dimensional image correlation on each of the image sets to determine deformation and strain data. The deformation and strain data from the image sets is stitched into one dataset. Principal strains, LoNEs directions, one or more LoNEs streamlines and lines of maximum and minimum extensions are determined. Visualizations for the strain magnitudes, LoNE streamlines, maximum and minimum extension streamlines are generated and provided in three dimensions. Based on one or more of the determined principal strains, the LoNEs directions, the one or more LoNEs streamlines and the lines of maximum and minimum extensions, a pattern is generated for one or more customized coverings for the test object. In an embodiment, the surface is human skin and the test object is a human, and wherein the one or more custom coverings comprise at least one of: custom garments, custom orthotics, custom prosthetics and custom wearable electronic devices. In an embodiment, the data collection system includes one or more stereoscopic camera pairs. In an embodiment, the data collection system includes at least one of: one or more optical cameras, computed tomography (CT) imager, and a magnetic resonance imager (MRI). In an embodiment, the data collection system includes one or more sensors in contact with the surface.

In yet another aspect, a non-transitory machine-readable storage medium is provided having encoded thereon program code, wherein, when the program code is executed by a machine, the machine implements a method for measuring surface deformation and strain using digital image correlation of a surface of a test object. The method includes acquiring images of the surface. The surface has a unique surface pattern to facilitate image acquisition. The images are grouped into one or more image sets. Three dimensional image correlation is performed on each of the image sets to determine deformation and strain data. The deformation and strain data from the image sets are stitched into one dataset. Principal strains and lines of non-extension (LoNEs) directions are determined. One or more LoNEs streamlines and lines of maximum and minimum extensions are determined. Visualizations for the strain magnitudes, LoNE streamlines, maximum and minimum extension streamlines are generated in three dimensions. Based on one or more of the determined principal strains, the LoNEs directions, the one or more LoNEs streamlines and the lines of maximum and minimum extensions, generating a pattern for one or more customized coverings for the test object. In an embodiment, the surface is human skin and the test object is a human, and wherein the one or more custom coverings comprise at least one of: custom garments, custom orthotics, custom prosthetics and custom wearable electronic devices.

BRIEF DESCRIPTION OF THE DRAWING FIGURES

Other aspects, features, and advantages of the claimed invention will become more fully apparent from the following detailed description, the appended claims, and the accompanying drawings in which like reference numerals identify similar or identical elements. Reference numerals that are introduced in the specification in association with a drawing figure may be repeated in one or more subsequent figures without additional description in the specification in order to provide context for other features.

FIG. 1A shows a diagram of a finite strain ellipse and FIG. 1B shows a diagram of Mohr's circle as employed by described embodiments;

FIG. 2 shows the strain ellipse of FIG. 1A in three cases: FIG. 2 case 1, shows a circle of material (solid lines) deformed (dashed lines) with compression and tension, FIG. 2 case 2 shows the circle deformed with tension in all directions, and FIG. 2 case 3 shows the circle deformed with compression in all directions;

DETAILED DESCRIPTION

Figure 1A:
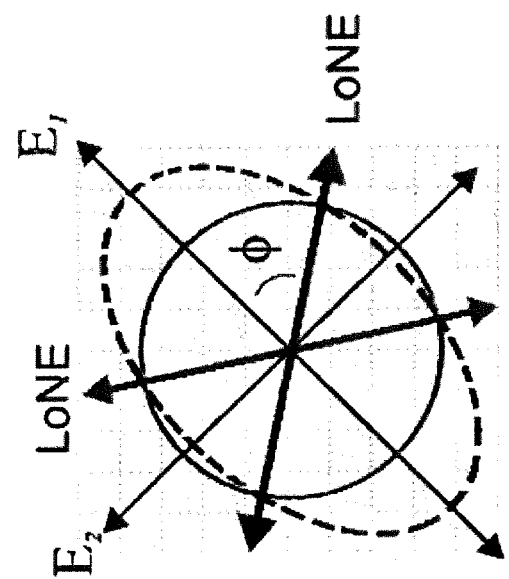

Table 1 summarizes a list of acronyms employed throughout this specification as an aid to understanding the described embodiments:

TABLE 1

| 2D | Two Dimensional | 3D | Three Dimensional |
|---|---|---|---|
| ABS | Acrylonitrile Butadiene Styrene | CAD | Computer Aided Design |
| CT | Computed Tomography | DIC | Digital Image Correlation |
| DAQ | Data Acquisition | FOV | Field of View |
| LIC | Line Integral Convolution | LoNEs | Lines of Non-Extension |
| MCP | Mechanical Counter Pressure | MRI | Magnetic Resonance Imaging |
| SLAM | Simultaneous Localization And Mapping | | |

There is a need to better understand the human body's natural skin strain field in order to drive the design of MCP space suits and the like that maximize mobility. By measuring the human skin strain field, materials and textile patterns can be developed to engineer a second skin-like garment that deforms similarly to skin and does not restrict mobility. For example, such garments might be advantageously employed in the design of mechanical counter pressure (MCP) space-suits and other compression garments. Using the skin strain field, Lines of Non-Extension (LoNEs) can be quantitatively analyzed and used to engineer garments such as an MCP suit. Techniques and systems described herein measure skin strain, calculate LoNEs, analyze the LoNE map of the entire body, and compare skin strain fields of multiple subjects.

Described embodiments employ two dimensional (2D) and three dimensional (3D) digital image correlation (DIC) to measure skin strain. Digital image correlation (DIC) is a non-contact optical technique to measure shape and deformation using digital vision, for example stereoscopic vision in the case of 3D DIC. Described embodiments use DIC to measure skin strain at a spatial resolution of less than 1 cm$^2$, and compute LoNEs from the collected strain data. Particularly, described embodiments successfully measure skin strain data at sub-pixel resolution of less than 1 mm$^2$.

Modelling the mechanical characteristics of human skin is an important aspect of developing skin-tight garments, such as an MCP space suit or other compression garments. Assessing skin deformation can be done using the "finite strain ellipse", which will be described in regard to FIGS. 1-3. The finite strain ellipse involves (1) placing a reference circle on the skin at an area under test in an initial static pose, and (2) moving the area under test into a deformed configuration. The initial circle deforms approximately into an ellipse, a smaller circle, or a larger circle, which can be measured in comparison to the original circle by placing the original circle on top of the deformed circle. Thus, the finite strain ellipse creates a circle and ellipse pair that can be analyzed. If the reference circle and deformed circle intersect, they form a pair of directions of non-extension. The directions of non-extension can be connected forming a contour map representing LoNEs, which are unique contours that do not extend during human motion.

In general, there can be an infinite number of LoNEs, although only a finite number of LoNEs are shown and analyzed to generate a contour map. Although termed lines of "non-extension," LoNEs might not remain an exactly constant length throughout a deformation, but because the LoNEs are similar throughout human motion, the contours typically change length on the order of 5 percent or less. LoNEs are not unique to a particular material, such as skin, and material properties do not cause LoNEs, although material properties can change LoNE patterns.

Deformation is the mapping of the reference state, X, to a deformed state, x by the function φ which can be expressed as:

$$x = \varphi(X) \tag{1}$$

The deformation gradient, F, is the gradient of the mapping from a deformed frame to a reference frame, given by:

$$F_{ij} = \frac{dr_i}{dX_J} = \begin{bmatrix} \frac{\partial r_1}{\partial X_1} & \frac{\partial x_1}{\partial X_2} & \frac{\partial x_1}{\partial X_3} \\ \frac{\partial r_2}{\partial X_1} & \frac{\partial x_2}{\partial X_2} & \frac{\partial x_2}{\partial X_3} \\ \frac{\partial r_3}{\partial X_1} & \frac{\partial x_3}{\partial X_2} & \frac{\partial x_3}{\partial X_3} \end{bmatrix} \tag{2}$$

After computing F, the Green-Lagrange and Euler-Almansi strain tensors can be computed. The Green-Lagrange strain, E, with respect to the reference geometry is given by:

$$E = \tfrac{1}{2}(F^T F - I) \tag{3}$$

and the Euler-Almansi strain, e, with respect to the deformed geometry is given by:

$$e = \frac{1}{2}((1-(FF^T)^{-1}) \qquad (4)$$

In the reference configuration, an angle from a line is denoted by φ, but in the deformed configuration, this angle changes to θ. The strains, E and e can be decomposed into eigenvalues and eigenvectors as given by:

$$E \cdot v = \lambda \cdot v \qquad (5)$$

The eigenvalues represent the principal strain magnitudes, $E_1$ and $E_2$, and the eigenvectors represent the direction in which the principal strain magnitudes are oriented. From the principal strain directions, the directions of non-extension are given by:

$$\phi = \tan^{-1}\left(\sqrt{-\frac{E_1}{E_2}}\right) \qquad (6)$$

where φ is the angle from the principal strain direction.

Figure 1B:
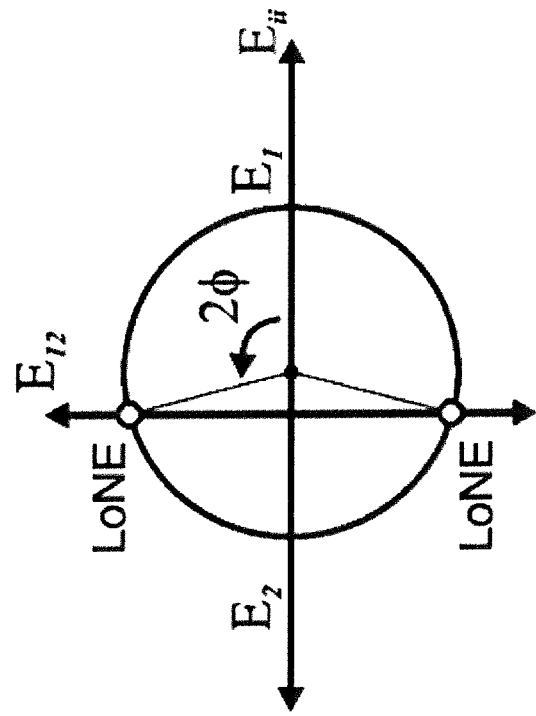

Referring to the finite strain ellipse shown in FIG. 1A and Mohr's circle shown in FIG. 1B, it can be shown that directions of non-extension exist if compression and tension are both present. As shown in FIG. 1A, when the solid line circle encounters principal strains $E_1$ and $E_2$, the circle is deformed into the dashed line ellipse. The dashed line ellipse shows that Lines of Non-Extension (LoNEs) develop where the two principal strains, $E_1$ and $E_2$, have opposite signs, which means the material is undergoing tension in one direction and compression in an orthogonal direction. There is no extensional strain along these lines, which is shown graphically in the ellipse and analytically in Mohr's circle. As shown on the finite strain ellipse shown in FIG. 1A and Mohr's circle shown in FIG. 1B, it is shown that the LoNE directions do not occur at the maximum shear directions, which is 450° from the principal strain. The direction of non-extension is denoted as φ.

Figure 2:
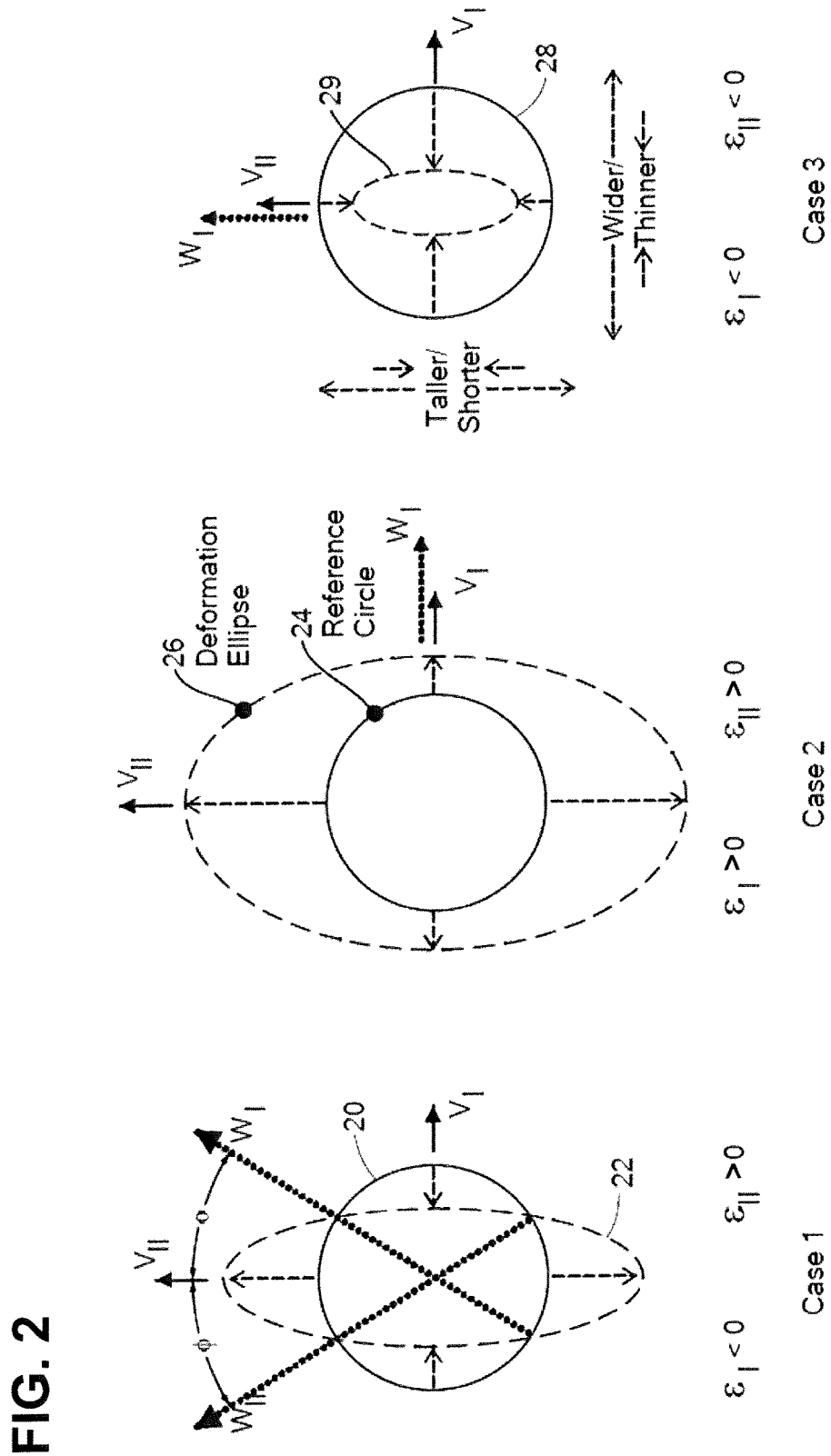

FIG. 2 shows three cases of deformation that can occur when considering the strain ellipse. As shown in FIG. 2, circle 20 is outlined in solid lines representing an initial position and ellipse 22 outlined in dashed lines represents a deformed position. As shown, an original circle of material is deformed in case 1 with compression and tension, case 2 with tension in all directions and case 3 with compression in all directions. Note that the directions of non-extension only exist in case 1 when there is both tension and compression. In case 2, reference circle 24 represents an initial position and the deformation ellipse 26 represents a deformed position. In case 2, complete extension is shown, such that the important direction is the line of minimum extension. In case 3, reference circle 28 represents an initial position and deformation ellipse 29 represents a deformed position. In case 3, complete compression is shown, such that the important direction is the line of minimum compression.

Figure 3:
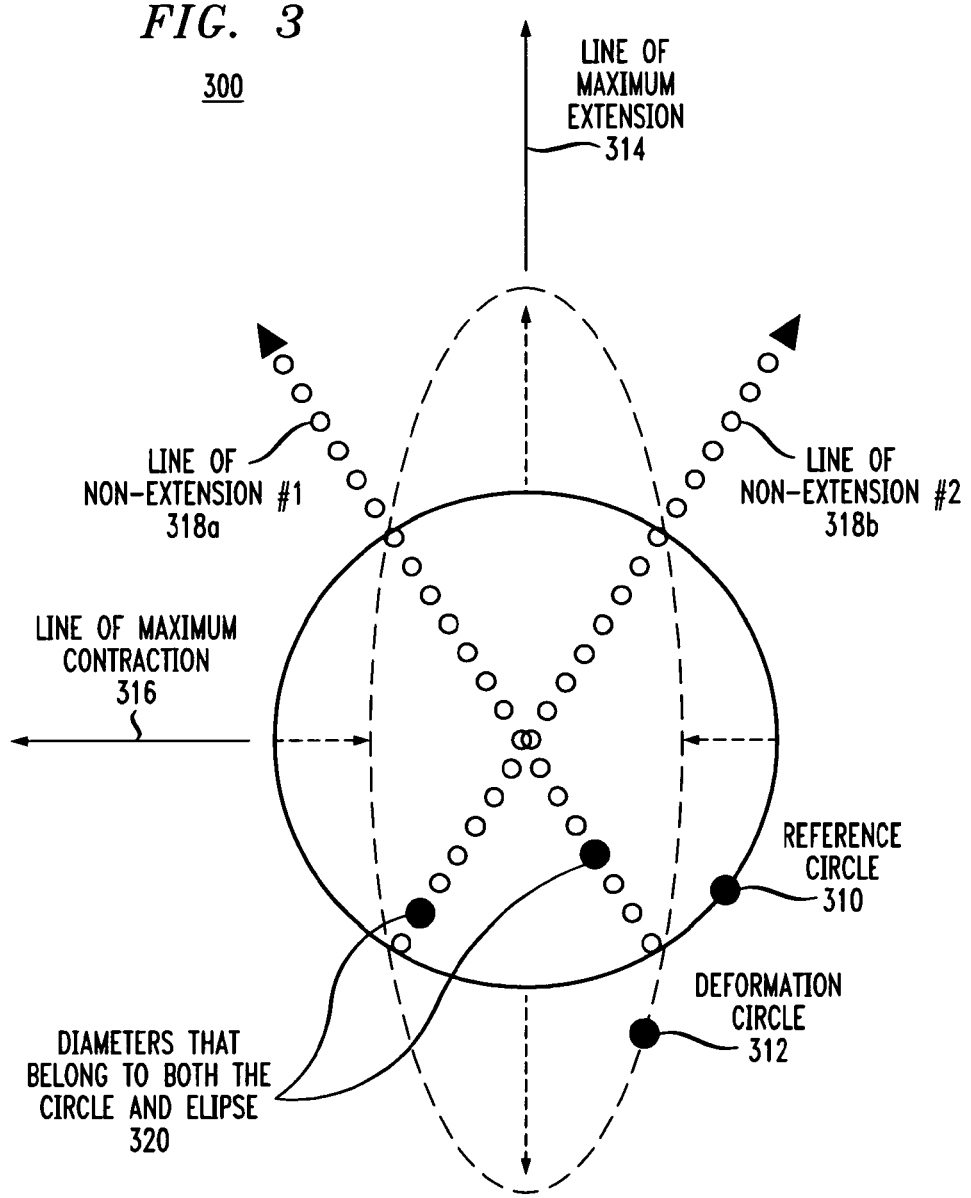
FIG. 3 is a graphical representation of Lines of Non-Extension (LoNEs) on a finite strain ellipse.

FIG. 3 shows a graphical representation of lines of non-extension includes a reference circle 310, a deformation circle 312, a line of maximum extension 314, a line of maximum contraction 316, and two lines of non-extension portions 318a and 318b that illustrate diameters belonging to both the circle and the ellipse.

Figure 4:
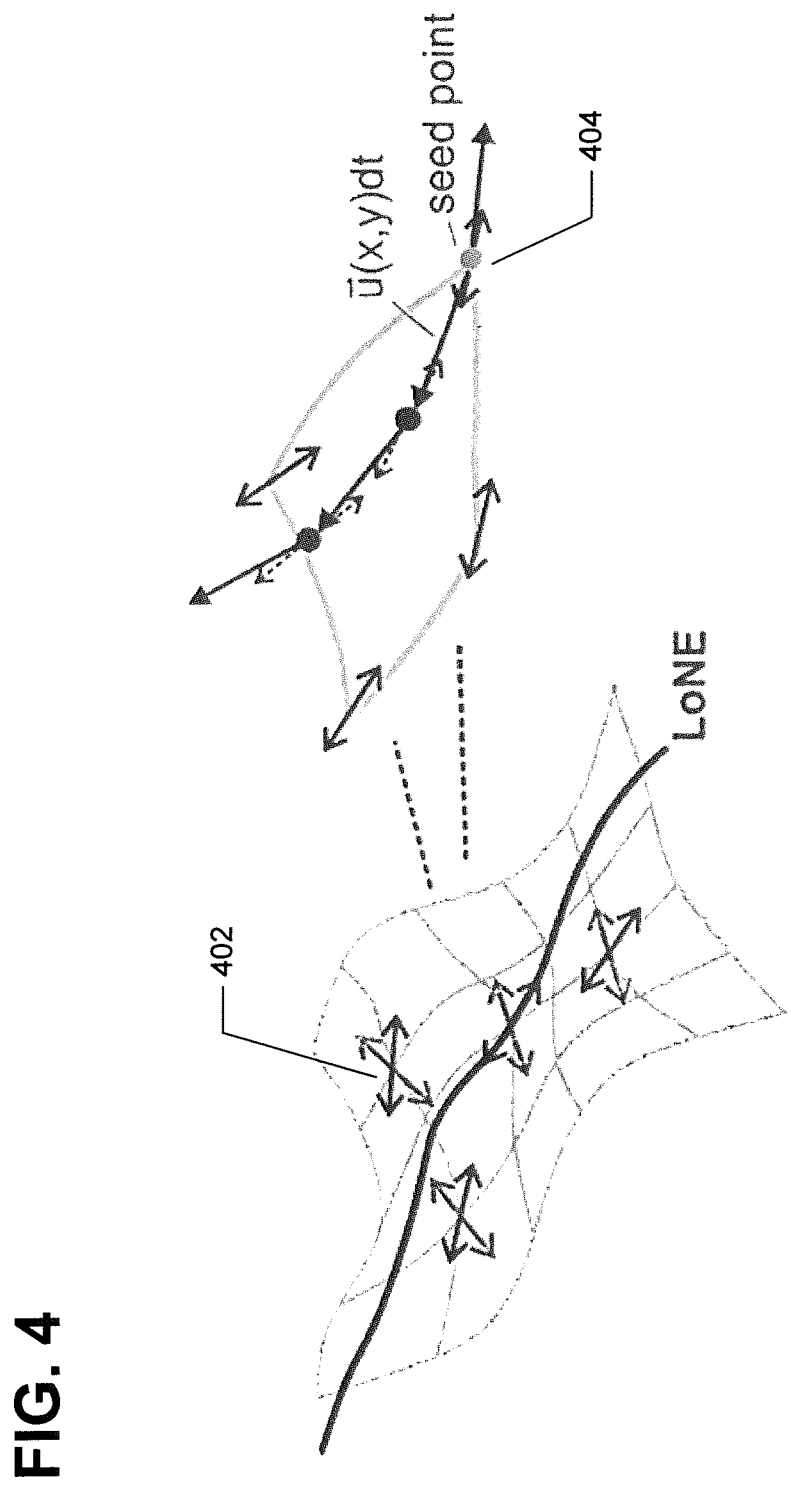
FIG. 4 is a graphical representation of LoNEs as streamlines based on vector fields and associated integration seed points.

LoNEs are contours along the surface of material that remains tangential to the non-extension direction. As shown in FIG. 4, if the LoNEs directions are treated as a vector field with constant magnitude, the numerical integration of this vector field produces streamlines tangential to the vector field. Since human skin has a thickness, but only surface deformation can be observed, a local coordinate system is used that is normal to the skin surface. The directions of non-extension can be considered an un-directed vector field with first and second directions of non-extension. To calculate the streamline a seed point, 404, is selected and each vector field is integrated from the seed point. The vector field is interpolated at each integration step, which allows the streamline to exist within each mesh element.

To generate LoNEs streamlines, various techniques of (1) vector field interpolation, (2) numerical integration, and (3) selection of seed points can be employed. For example, a bilinear interpolation or basis splines (or b-splines) vector field interpolation technique might be employed. Similarly, for numerical integration, numerical integration, Euler's technique or the Runge-Kutta technique might be employed.

Using numerical integration, the interpolated vector field is used to determine streamlines where the new position is the current position plus the velocity at that point multiplied by a time step or spatial parameter, dt. Since human skin has a thickness, the vector field lies along a surface and is not completely 2D or completely 3D. Thus, the integration is performed using a local 2D coordinate system that is transformed for each position to a 3D coordinate system, for example by:

$$X'_i = R^{-1} X_i$$

$$X'_{i-1} = X'_i + \bar{u}(X'_i)dt$$

$$X_{i+1} = R X'_{i-1} \qquad (7)$$

Numerical integration techniques applied to seed points produce numerical space curves defined by Cartesian coordinates, which is useful for computer-aided design (CAD) of garments, for example an MCP space suit. In alternative embodiments, surface Line Integral Convolution (surface LIC) might be employed to produce rasterized textures on the surface, by convolving a noisy image with a vector field. Unlike numerical integration, surface LIC allows visualization of the entire vector field instead of only streamlines that connect to seed points.

Figure 5:
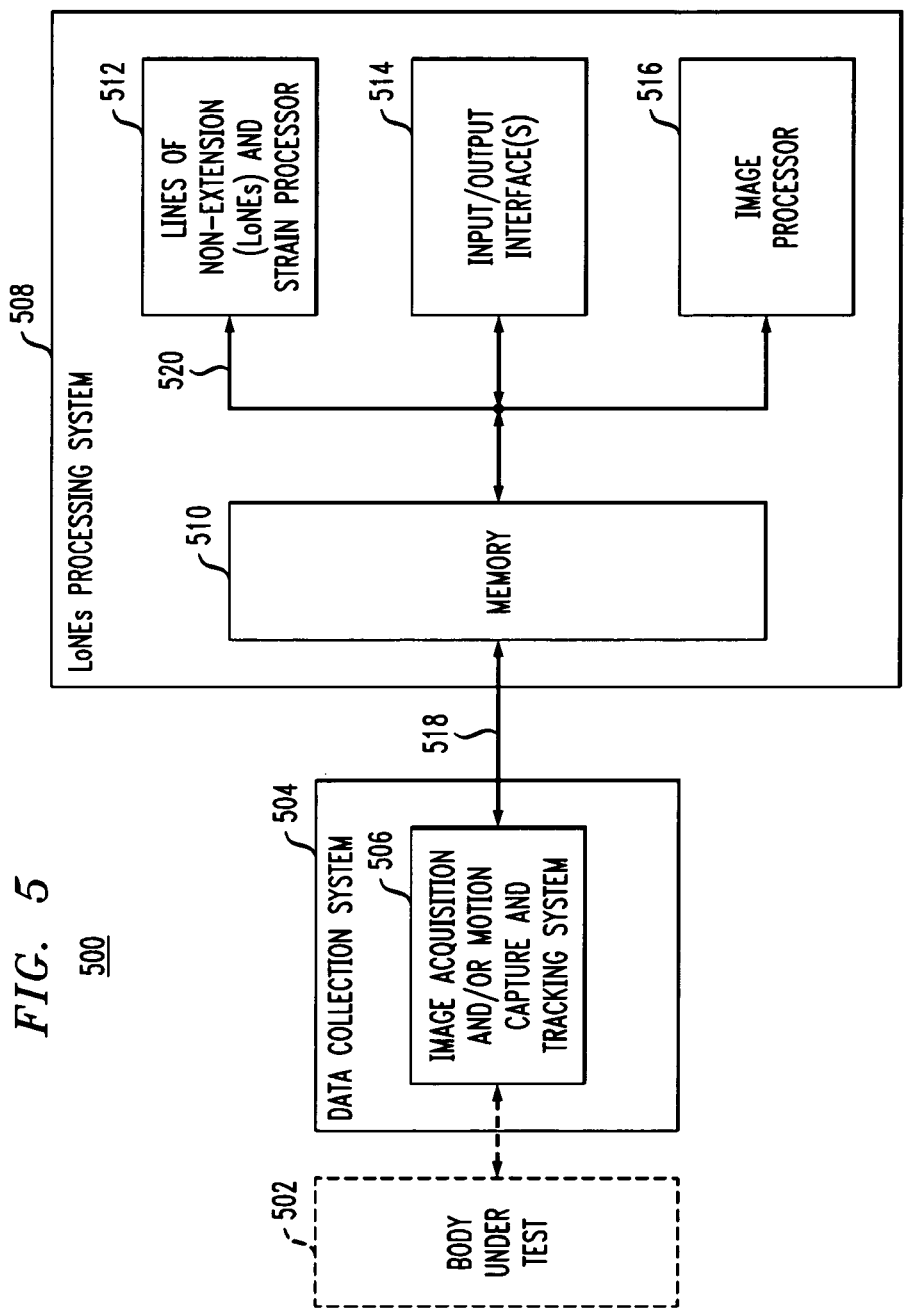
FIG. 5 is a block diagram of an illustrative system to process digital image correlation data, measure and model skin movement, and determine strain fields, contours and three-dimensional patterns in accordance with described embodiments.

Described embodiments measure deformation and strain of human skin using digital image correlation (DIC). FIG. 5 shows a block diagram of an illustrative system for capturing and processing digital image correlation data, measuring and modeling skin movement, and determining strain fields, contours and 3D patterns, shown as system 500. System 500 includes data collection system 504 to capture information about a body under test 502. For example, data collection system 504 includes image acquisition or motion capture and tracking system 506. Data collection system 504 is in communication with LoNEs processing system 508. LoNEs processing system 508 includes one or more processors, shown as 512 and 516, to process data from data collection system 504. For example, LoNEs processor 512 determines strain and LoNEs data, for example LoNEs streamlines, based on data communicated from data collection system 504 for body under test 502. Similarly, image processor 516 might process image data collected from data collection system 504 for body under test 502.

Data might be transferred between data collection system 504, processors 512 and 516, and input/output (I/O) interfaces 514 by one or more communication links 518 and 520 and stored in memory 510. Communication links 518 and 520 might be any suitable communication interface, for example a physical transmission medium such as a backplane, optical fibers, coaxial cables, twisted pair copper wires, or a wireless transmission medium such as one or more radio frequency (RF) channels or one or more infrared (IR) channels. Further, communication links 518 and 520 might employ any communication protocol over the transmission medium, for example, by operating in accordance with a custom communication protocol, or operating in accordance with standard communication protocols such as a Small Computer System Interface ("SCSI"), Serial Attached SCSI ("SAS"), Serial Advanced Technology Attachment ("SATA"), Universal Serial Bus ("USB"), Ethernet, IEEE 802.11 ("WiFi"), IEEE 802.15, IEEE 802.16, IEEE 1394 ("Firewire"), Peripheral Component Interconnect Express ("PCI-E"), Serial Rapid I/O ("SRIO"), Infrared Data Association (IrDA), GigE Vision, Camera Link, CoaXPress ("CXP"), Digital Visual Interface ("DVI"), High-Definition Multimedia Interface ("HDMI"), or any other similar interface protocols for communicating data between computers and computer components. Although not shown in FIG. 5, memory 510 might include both volatile and non-volatile storage elements, for example, non-volatile elements including solid-state media, optical media, magnetic media, or hybrid solid-state and magnetic media, and volatile elements including static random-access memory (SRAM) or dynamic random-access memory (DRAM).

Figure 6:
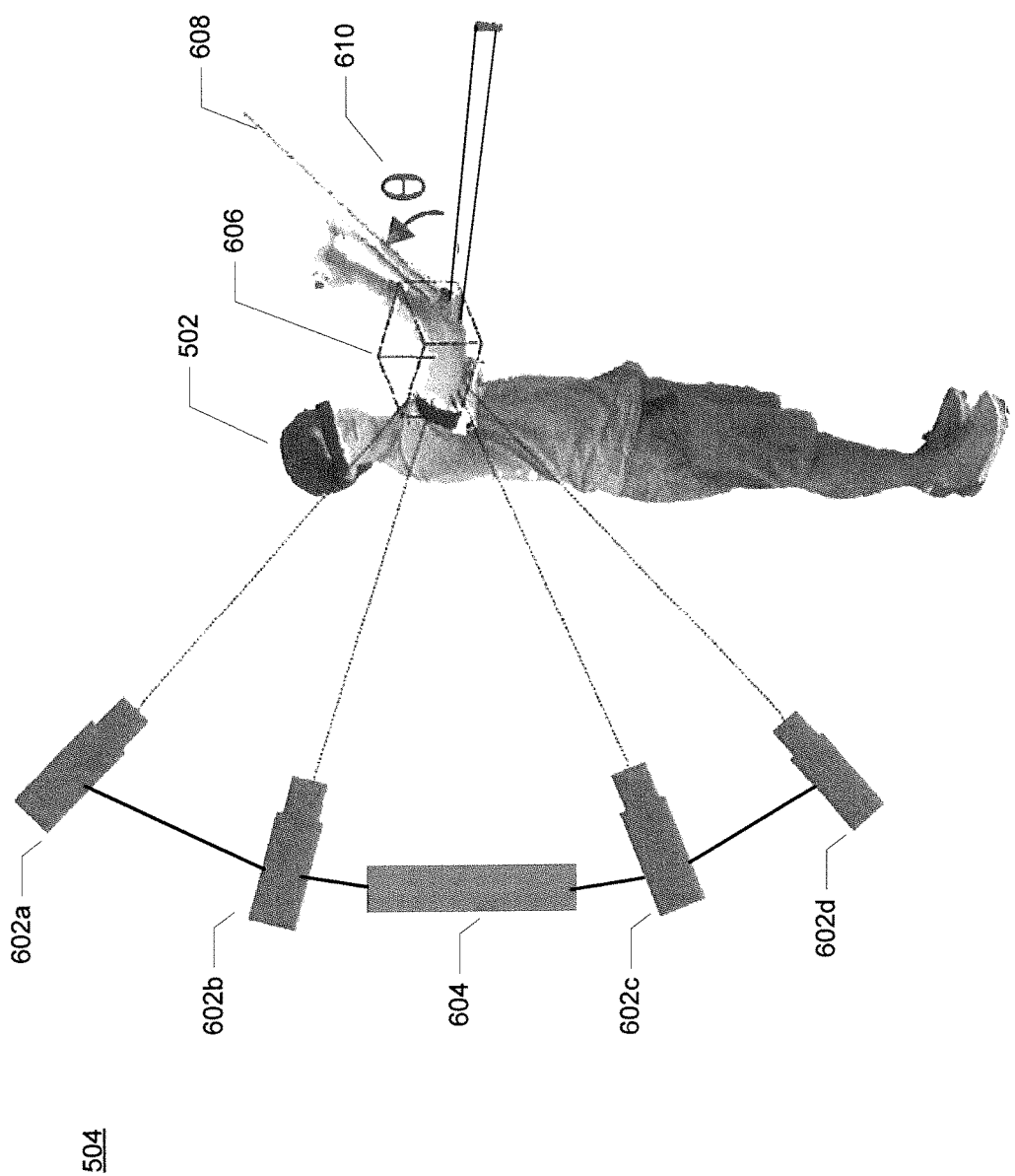
FIG. 6 is a diagram showing a illustrative test setup to capture digital image correlation data in accordance with described embodiments.

FIG. 6 shows greater detail of data collection system 504 and body under test 502. As shown in FIG. 6, an illustrative embodiment of data collection system 504 for performing digital image correlation includes a plurality of cameras shown as cameras 602a-602d. Although shown in FIG. 6 as including 4 cameras, any suitable number of cameras might be employed depending on the range of motion to be monitored. Lamp 604 illuminates region of interest 606. Similarly, although shown in FIG. 6 as including 1 lamp, any suitable number of lamps might be employed depending on the range of motion to be monitored and desired resolution of captured images. Cameras 602a-602d are disposed to focus on a specific region of interest 606 of body under test 502, for example the human elbow as shown. In the embodiment shown in FIG. 5, cameras 602a-602d are disposed in an arc such that an approximately 180° view of region of interest 606 is captured by data collection system 504.

Each of cameras 602a-602d beneficially employ a lens having a relatively small focal length (e.g., 16 mm) with low-distortion to provide a large field of view (FOV) of region of interest 606. In other embodiments, a larger focal length lens might be employed to increase the resolution of captured images of region of interest 606. The field of view (FOV) is given by:

$$FOV = \frac{(\text{sensor size}) \times (\text{distance to object})}{\text{focal length}} \quad (8)$$

In some embodiments, to facilitate operation of cameras 602a-602d as a multiple-view camera system simultaneously imaging region of interest 606, cameras 602a-602d are synchronized, for example, by hardware or software triggering for data acquisition (DAQ).

As shown in FIG. 6, data collection system 504 also includes test rig 608, which allows region of interest 606 of body under test 502 to move in a predetermined manner with a predetermined range of motion, thereby reducing variability between test subjects or between tests. Test rig 608 might also align a test subject in a known position for data collection system 504 to perform DAQ. For example, in the embodiment shown in FIG. 6, test rig 608 allows the elbow of a test subject to move over a predetermined range of motion, indicated by angle θ, and aligns the test subject at a known distance from, and in a known orientation with regard to, cameras 602a-602d.

Figure 7:
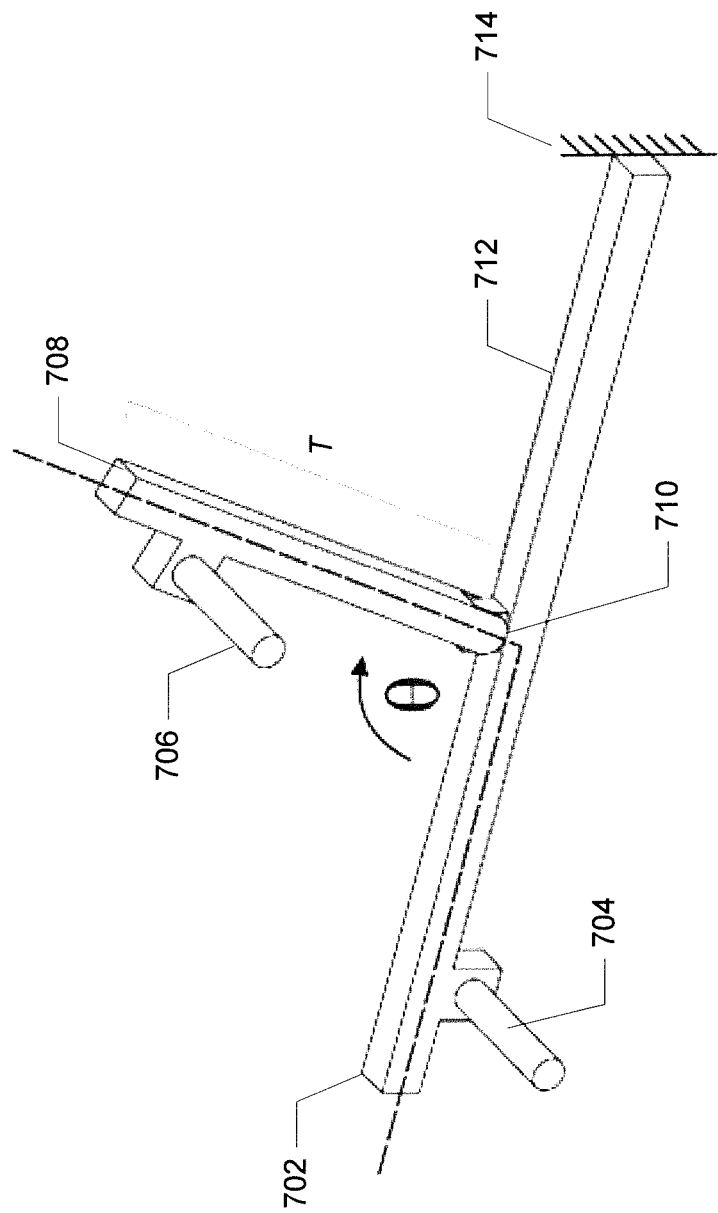
FIG. 7 is an isometric view of a test movement device in accordance with described embodiments.

FIG. 7 shows test rig 608 in greater detail. Although the test rig shown in FIG. 7 is configured to position and test an elbow joint of a test subject, other rig constructions are possible to test other joints. As shown, test rig 608 includes two support members, 702 and 708, that pivot via hinge 710. Test rig 608 is movable over a range of motion to allow measurement of the test subject's elbow joint angle, θ. Test rig 608 might be positioned attached to a wall or other structure (714) by support member 712 that allows a full range of motion for the test subject while also supporting the weight of test rig 608 itself. Test rig 608 includes grips 704 and 706 to support the test subject's hand and upper arm. For example, the upper arm of a test subject rests on bottom grip 704 and top cylinder 706 is used for hand placement during right arm testing. Test rig 608 could also be adapted for left arm testing.

Figure 8:
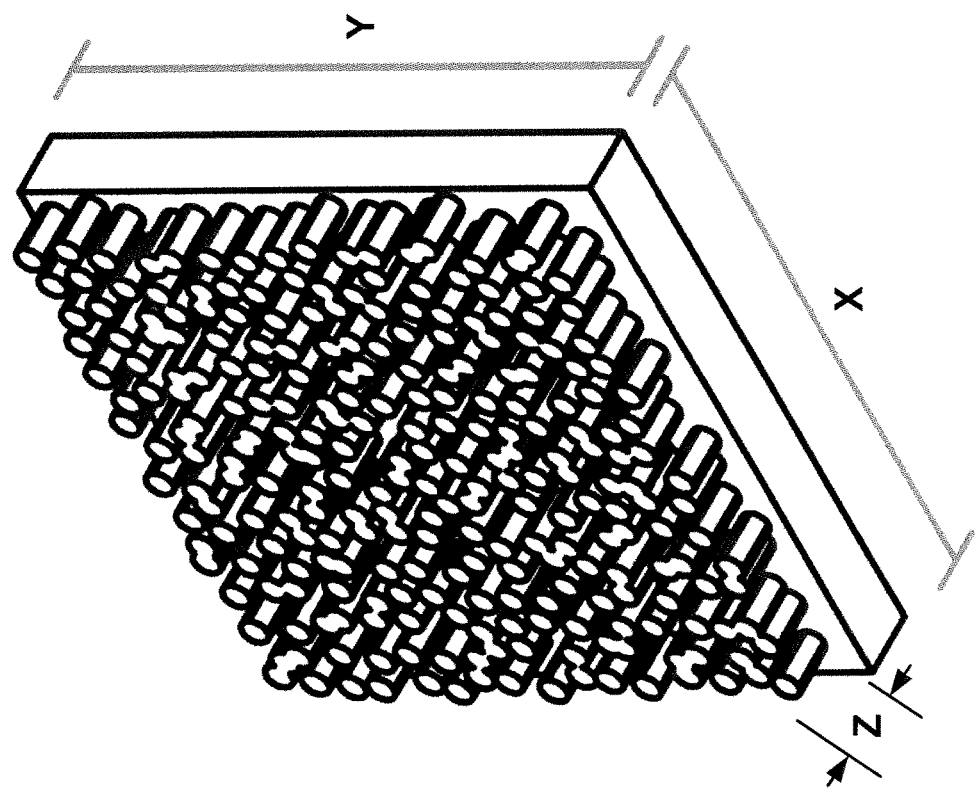
FIG. 8 is an isometric view of a three dimensional (3D) stamp to produce the unique surface texture shown in FIG. 9.
Figure 9:
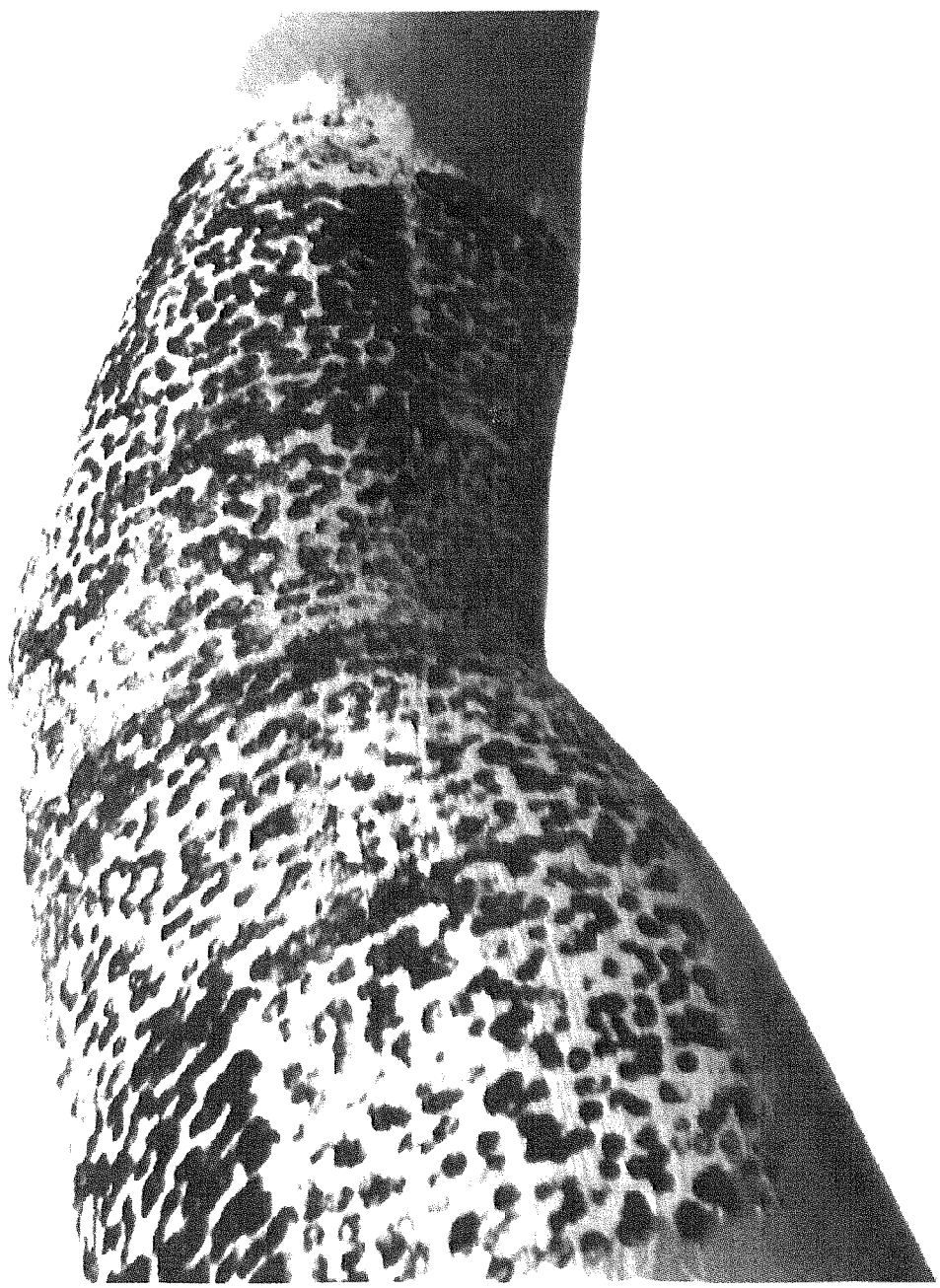
FIG. 9 is a diagram illustrating a unique surface texture employed to perform 3D digital image correlation in accordance with described embodiments.

For system 500 to generate strain data using 3D DIC, a unique and sufficiently random surface texture or speckle pattern is generated to enable data collection system 504 to capture skin locations (e.g., deformations) over an observed range of motion. FIG. 8 shows a view of 3D printed pattern stamp 800 used to apply a 3D speckle pattern to region of interest 606. For example, a base color (e.g., natural skin tone, a sufficiently skin-tight garment such as a motion capture suit, or a base paint color applied to the skin) of region of interest 606 is covered with a second color using 3D printed pattern stamp 800. 3D printed pattern stamp 800 might be 3D printed out of ABS plastic or machined out of other materials. An example of the applied speckle pattern on skin at the elbow of a test subject is shown in FIG. 9.

Figure 10:
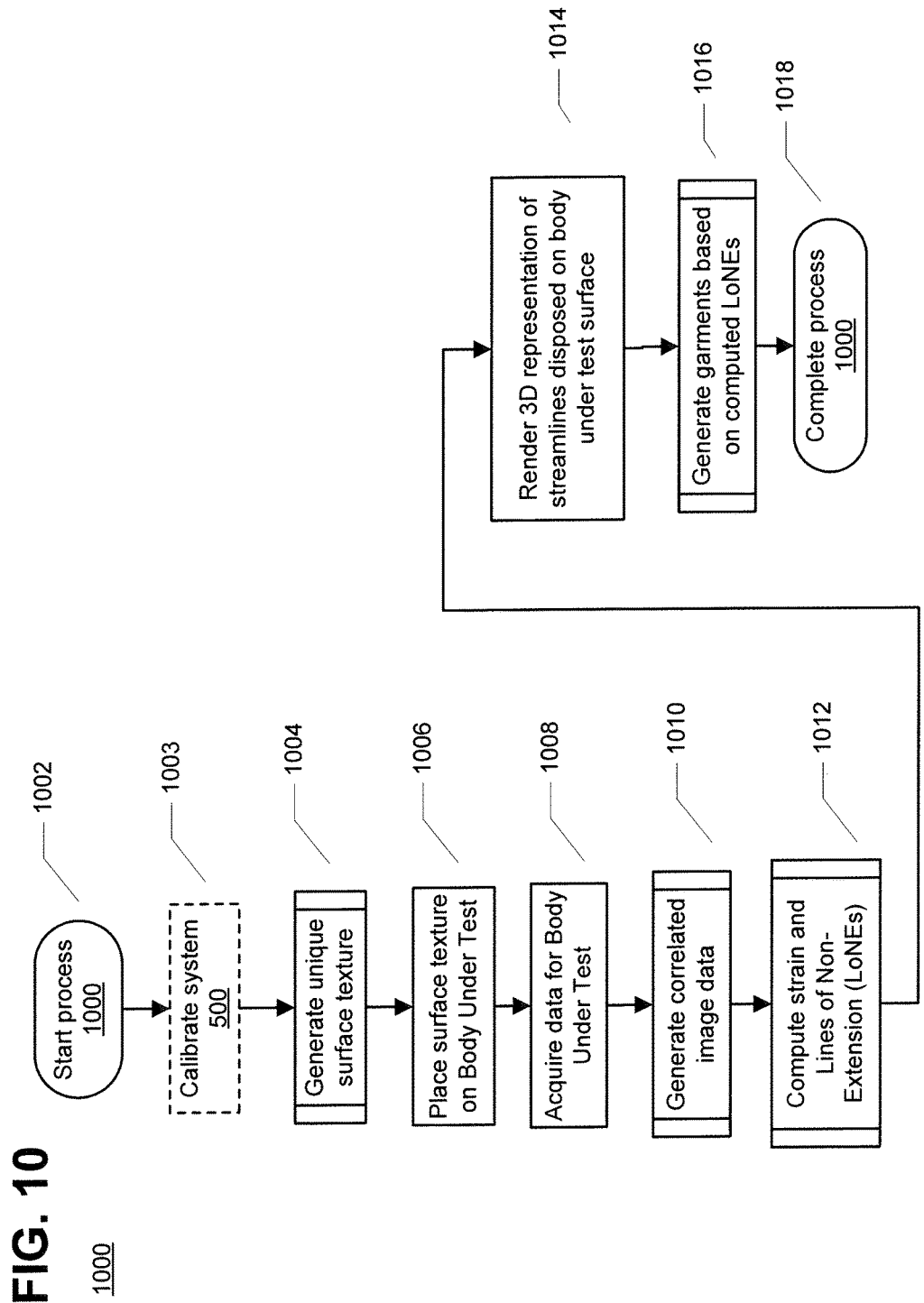
FIG. 10 is a flow diagram showing an illustrative process for generating LoNEs based on captured image data in accordance with described embodiments.

FIG. 10 shows a flow diagram of 3D DIC process 1000. At block 1002, process 1000 starts, for example by gathering data about the test subject(s) and region of interest 606 for each test subject. For example, to measure skin deformation and strain at the elbow joint of the human body for six test subjects, age and anthropometric data might first be determined, for example as shown in Table 2. Forearm length is measured from the lateral epicondyle to the styloid process of ulna, upper arm length is measured from the acromion to the lateral epicondyle, and bicep and forearm circumference is measured at the largest circumference along the limb. All dimensions are in cm.

TABLE 2

| n = 6, age: µ = 23.2 years, σ = 2.8 years | | | | | | |
|---|---|---|---|---|---|---|
| Subject | A | B | C | D | E | F |
| Forearm length | 26.5 | 29 | 24 | 24 | 24 | 24 |
| Upper arm length | 34 | 33 | 28.5 | 32 | 29 | 33 |
| Bicep circumference (relaxed) | 31 | 29 | 22.5 | 29 | 28 | 29 |
| Bicep circumference (flexed) | 34 | 32 | 24 | 30.4 | 28 | 30 |
| Forearm circumference | 27 | 25.5 | 19.5 | 26.5 | 27 | 26 |

At block 1003, data collection system 504 is calibrated using a known pattern of a known size, to determine the optical properties of cameras 602a-602d and the stereoscopic geometry. At block 1004, a unique surface texture or speckle pattern is generated and stamp 800 is generated according to the generated texture or pattern. Block 1004 will be described in greater detail in reference to FIG. 11. At block 1006, stamp 800 is used to apply the texture or pattern to region of interest 606 of the test subject.

At block 1008, image or motion data is captured by data collection system 504. Cameras 602a-602d remain fixed throughout the data collection period so multiple calibrations were not necessary and all data could be collected in the same coordinate system. For the illustrative case of testing an elbow of the test subject, each test subject places their arm on test rig 608 and positions their arm at predetermined angle increments throughout the range of motion of their elbow. Thus, a full range of elbow and flexion and extension can be captured by data collection system 504 for each test subject. For example, test subjects might position their arm in increments of 15°, starting at 0° elbow flexion to their maximum elbow flexion angle, which is typically approximately 135°. All subjects keep their palms facing upward throughout elbow flexion so that musculature is similar throughout the motion and between test subjects.

To process data from many cameras, some embodiments might employ simultaneous localization and mapping (SLAM) such as used by autonomous vehicles to map the environment. Further, as joints, such as the elbow, flex beyond 90°, the skin starts to buckle and fold such that strain cannot be measured using DIC. Thus, some embodiments might further employ wearable sensors to measure deformation within buckles and folds. Although described herein as employing optical DIC, optical DIC can only measure in-plane surface deformation because it can only see the surface of the object. Thus, some embodiments might employ computed tomography (CT), ultrasound, magnetic resonance imaging (MRI) or other similar technologies to measure out-of-plane skin deformation as "volumetric" DIC.

At block 1010, 3D digital image correlation is performed. During 3D DIC, LoNEs processing system 508 determines the displacement of pixel subsets in stereoscopic pairs of images captured by data collection system 504. Block 1010 will be described in greater detail in reference to FIG. 12. At block 1012, the determined pixel subset displacements are used to calculate the strain of the surface. For example, a subset of N pixels from images captured by a subset of M of cameras 602a-602d might be used to generate correlated image data and calculate strain data. In an illustrative embodiment, a subset of 71 pixels (N=71) might be used with a step size of 7 pixels to correlate image data from a subset of cameras 602a-602d. Further, in some embodiments, the image correlation might be performed for stereoscopic camera pairs (e.g., cameras 602a and 602b, and 602c and 602d for the example 4 camera system shown in FIG. 6). At block 1012, Green-Lagrange strain and/or Euler-Almansi strain is calculated. Block 1012 will be described in greater detail in reference to FIG. 13.

At block 1014 the strains and LoNEs are used to render 3D streamlines onto the surface of the body under test. Described embodiments treat the LoNEs directions as a vector field and integrate the vector field as streamlines tangential to the surface. Because the vector field is not technically a velocity field, the time step used in the integration is not technically a time step, but can be considered a spatial parameter. Interpolating the vector field at each time step determines the vector field at the integration point. To linearly interpolate the vector field, the S nearest neighbors are transformed to the local tangential coordinate system by:

$$S' = R^{-1}S$$

$$S' = S' - \langle S' \rangle \tag{9}$$

Once the S nearest neighbors are in the local coordinate frame, they are used to bilinearly interpolate the components of the vector field, u, using a least-squares approach, given by:

$$u(x,y) = a + bS'_x + cS'_y + dS'_xS'_y \tag{10}$$

$$u(x,y) = \begin{bmatrix} 1 & S'_{x1} & S'_{y1} & S'_{x1}S'_{y1} \\ \vdots & \vdots & \vdots & \vdots \\ 1 & S'_{xk} & S'_{yk} & S'_{xk}S'_{yk} \end{bmatrix} = a$$

$$u(x,y) = Aa$$

$$\tilde{a} = (A^TA)^{-1}A^Tu(x,y)$$

$$\tilde{u}(x,y) = \tilde{a} + \tilde{b}x + \tilde{c}y + \tilde{d}xy$$

where $\bar{u}(x,y)$ is the interpolated vector field.

This interpolated vector field is used to determine streamlines where the current position plus the velocity at that point multiplied by the time step is the new position. Since the vector field lies along a surface and is not completely 2D or completely 3D, integration is performed using a local 2D coordinate system and transforming the coordinates to 3D, as given by:

$$X'_i = R^{-1}X_i$$

$$X_{i+1} = X'_i + \bar{u}(X'_i)dt$$

$$X_{i+1} = RX'_{i+1} \tag{11}$$

Figure 14:
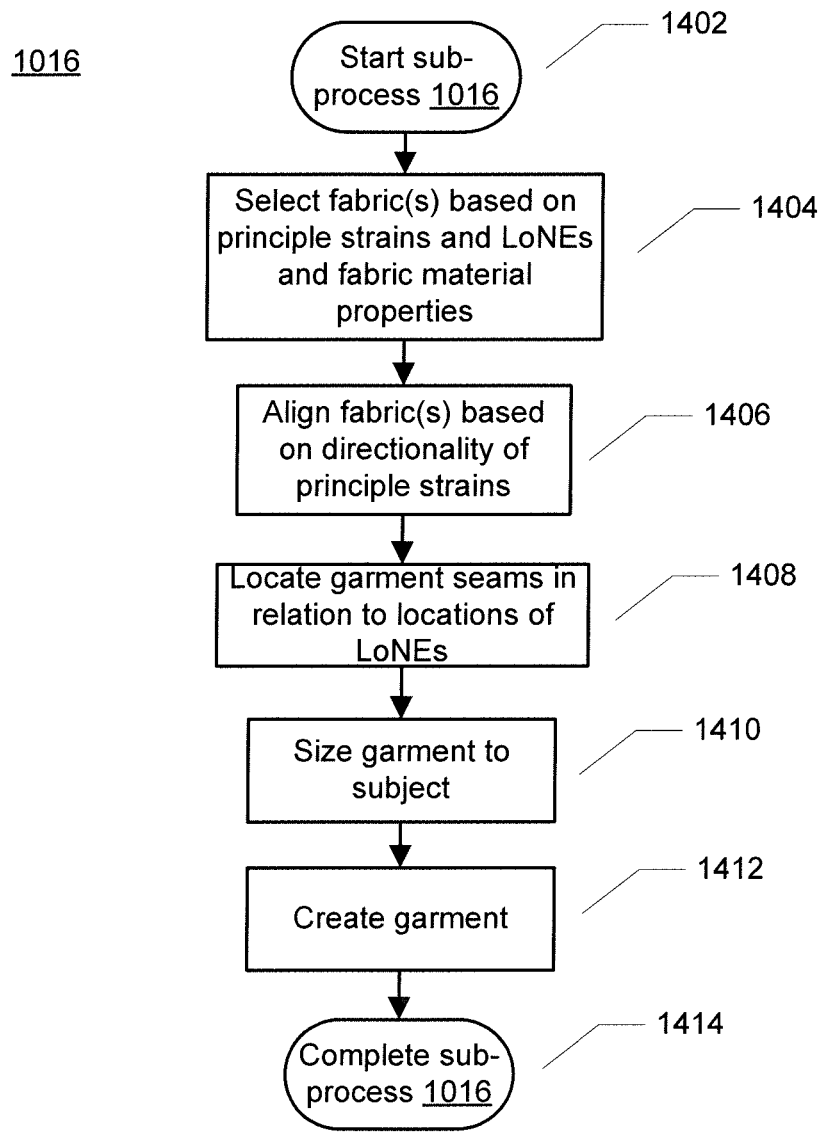
FIG. 14 is a flow diagram showing an illustrative process of generating a garment based on determined LoNEs in accordance with described embodiments.
Figure 15:
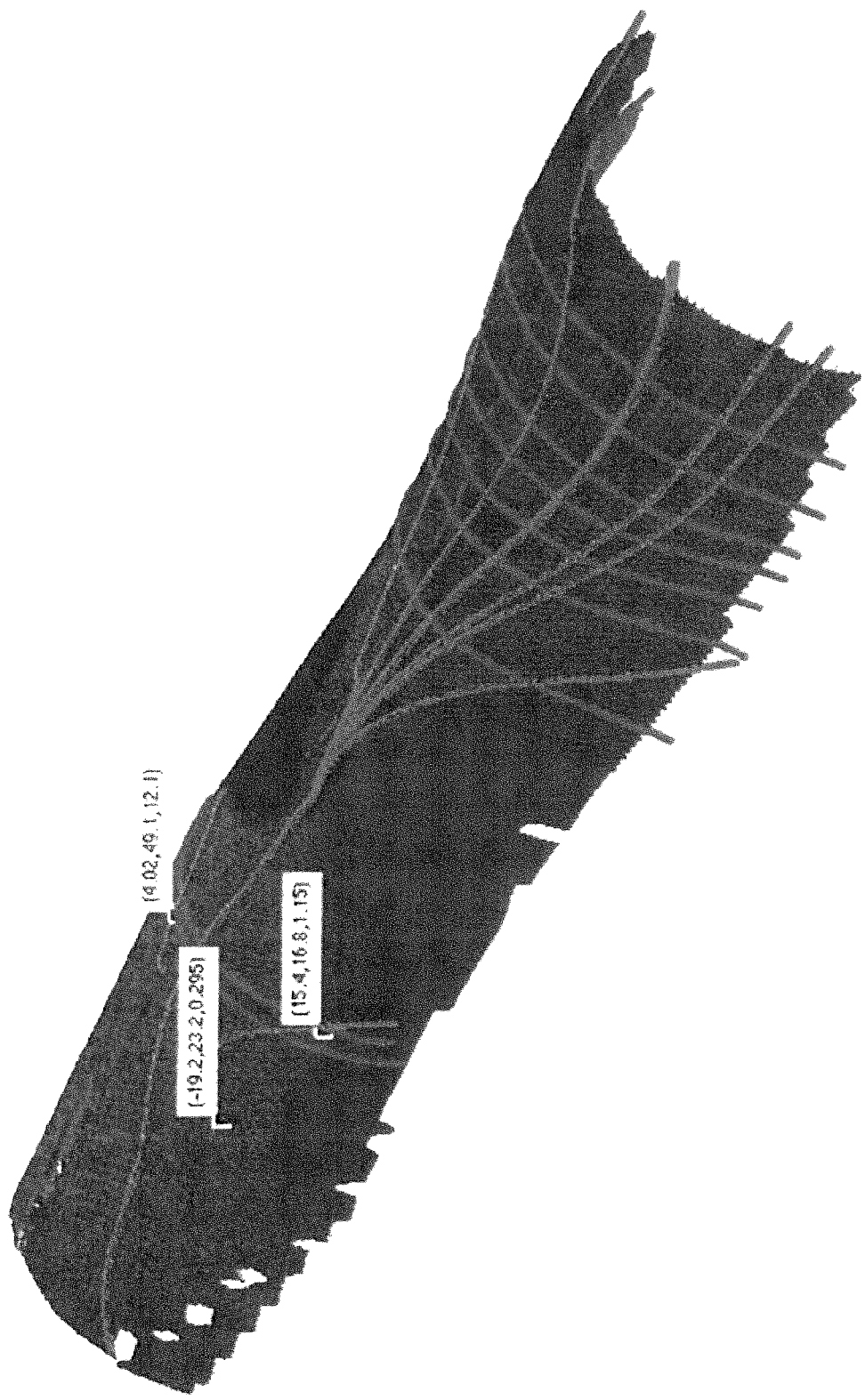
FIG. 15 is a diagram showing an illustrative seed point streamline vector field in accordance with described embodiments.

An illustrative projection of LoNEs streamlines projected onto an arm of a body under test is shown in FIG. 15. At block 1016 the generated strains, LoNEs and streamlines are employed to generate garments or garment pieces. Block 1016 will be described in greater detail in reference to FIG. 14. At block 1018, process 1000 completes.

Figure 11:
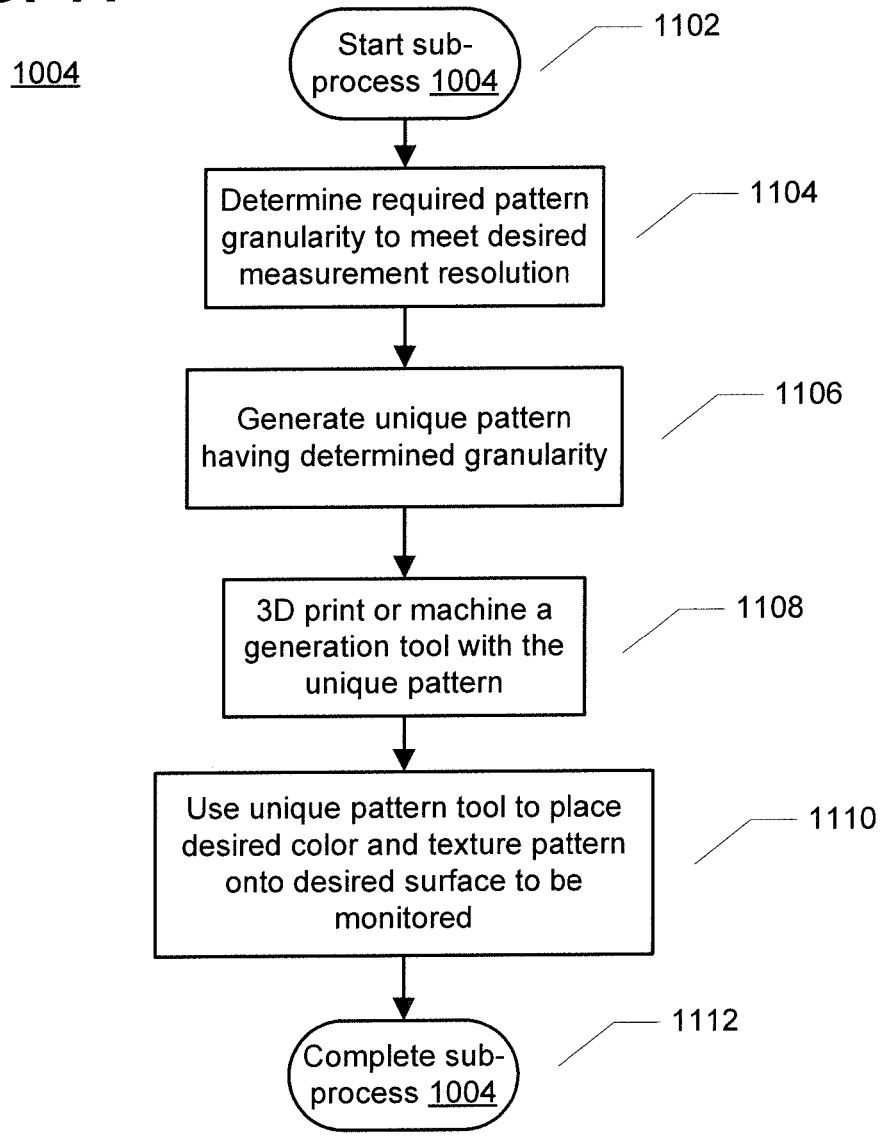
FIG. 11 is a flow diagram showing an illustrative process for generating a unique surface textures for capturing image data in accordance with described embodiments.

FIG. 11 shows additional detail of block 1004 of FIG. 10. At block 1102, sub-process 1004 begins. At block 1104, the required pattern or texture granularity to meet a desired measurement resolution is determined. At block 1106, a unique pattern or texture having the required granularity is generated. At block 1108, a pattern application tool, such as stamp 800 shown in FIG. 8, is 3D printed or machined out of an appropriate material, such as ABS plastic. For example, as shown in FIG. 8, the granularity of the pattern application tool might be determined by the size or radius of pattern textures 802 in the X-Y plane and the varying heights of pattern textures 802 in the Z-plane. At block 1110, the generated pattern application tool is used to place a desired color, texture and/or pattern onto the skin (or other desired surface) to be monitored. At block 1112, sub-process 1004 completes.

Figure 12:
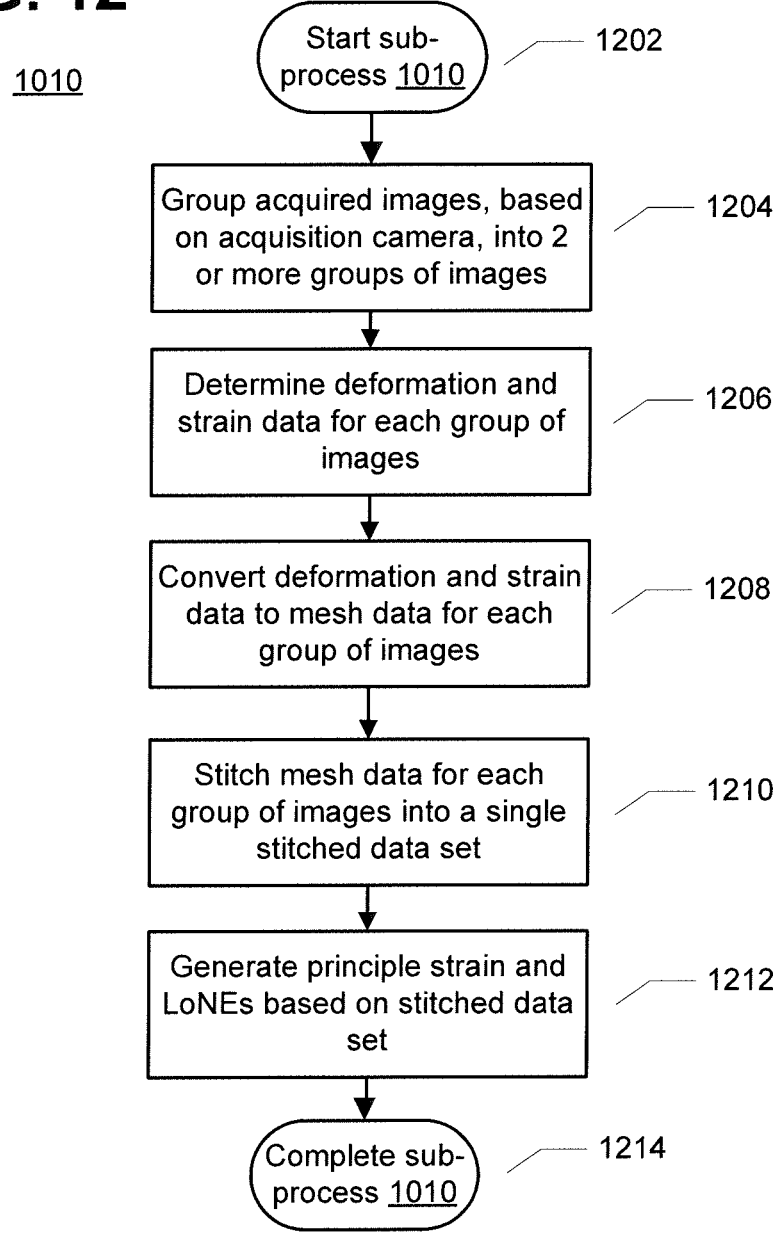
FIG. 12 is a flow diagram showing an illustrative process for correlating captured image data in accordance with described embodiments.

FIG. 12 shows additional detail of block 1010 of FIG. 10. At block 1202, sub-process 1010 begins. As described herein, data collection system 504 obtains data at various monitored positions of a body under test. As shown in FIG. 6, in one embodiment, the measurement system includes a motion capture system (including, for example, a set of cameras, video acquisition, processing and tracking markers such as a speckle pattern or texture). In other embodiments, other tracking systems might be employed, such as a laser scanner, to record body positions and movements and motions either while the body under test is in motion (dynamic) or in a fixed position (static or stationary).

At block 1204, motion data, for example image data captured by cameras 602a-602d, is grouped, for example into images datasets for stereoscopic camera pairs. The data analysis process consists of optical computer vision techniques, mechanics, mesh stitching and 3D visualization to (1) determine strain using 3D DIC (e.g., block 1206), (2) stitch datasets together from multiple stereoscopic camera pairs (e.g., block 1210), and (3) calculate LoNEs (e.g., block 1212). Digital image correlation calculates the full strain field of the surface of the object, which in turn can be used to calculate the LoNEs.

Digital image correlation does not track the motion of individual speckles or texture points, but rather performs correspondence tests between images by finding matching image subsets. The speckle pattern provides a unique texture and pattern to ensure that image subsets are matched correctly. Each subset corresponds to a single data point in Cartesian space. As these subsets are followed throughout the deformation, a strain calculation can be performed on each point by determining the deformation gradient. Particularly, a stereoscopic correspondence is performed to triangulate each image subset to determine the 3D location of the subset on the actual body under test. A deformation correspondence is performed between the reference frame and the deformed frame. Once a correspondence is made between all the frames a strain calculation can be performed to determine the deformation gradient of all corresponding points.

At block 1206, deformation and strain data is determined for each image dataset. In one embodiment, the deformation and strain is determined as curvilinear grid data. At block 1208, the stereoscopic datasets are converted from the acquired data type into a mesh data type. In one embodiment, the mesh data type might be a triangular mesh including vertices and triangular faces. At block 1210, the meshes for each of the stereoscopic datasets are stitched together at their overlap. Thus, at block 1212, the datasets from all of cameras 602a-602d can be analyzed as a single dataset.

When the data capture is performed using one or more stereoscopic camera pairs, the data from the multiple stereoscopic camera pairs is combined into a single dataset at block 1210. It is easiest to combine the camera pair datasets when the datasets are in the same coordinate system, which can be achieved by setting the global coordinate system of each stereoscopic camera pair to a coordinate system defined by the calibration board seen in the first frame of all cameras. As described herein, at block 1208, the datasets for each stereoscopic camera pair might be converted to mesh data having vertices and triangular faces. The meshes are stitched together at their overlap.

When there is data overlap between the meshes, there are three possible techniques to combine the datasets: (1) keep all of the data and merge the data sets by re-meshing the data at the overlap, (2) averaging the overlapping data, or (3) only keeping data that meets a certain criteria. Option (1) can cause the surface to be rough at the overlap. Option (2) can introduce uncertainty in the data by averaging quantities that do not exactly overlap. Option (3), despite discarding data, does not introduce uncertainty and also can maintain a smooth surface transition at the overlap. In embodiments employing option (3) (e.g., discarding some of the overlapping data), a measurement quality index, q, is selected to determine which data to discard, where q is defined as the inverse of the standard deviation of the matching error, $q=1/\sigma$. As q increases, the dataset matching error decreases. Typically, the quality decreases closer the edge of each dataset, and the magnitude of quality from the datasets will eventually intersect such that data with the higher quality is kept. Thus, at block 1210, the two datasets are then stitched together by discarding data from each dataset that has a lower value of q.

At block 1212, the strain fields are calculated using a local two dimensional coordinate system and the out-of-plane strain components, $E_{13}$, $E_{23}$, $E_{33}$, are assumed to be zero. The strain tensor $$E = \begin{bmatrix} E_{11} & E_{12} \\ E_{12} & E_{22} \end{bmatrix} \quad (12)$$

becomes 2D in the local coordinate system. At block 1214, sub-process 1010 completes.

Figure 13:
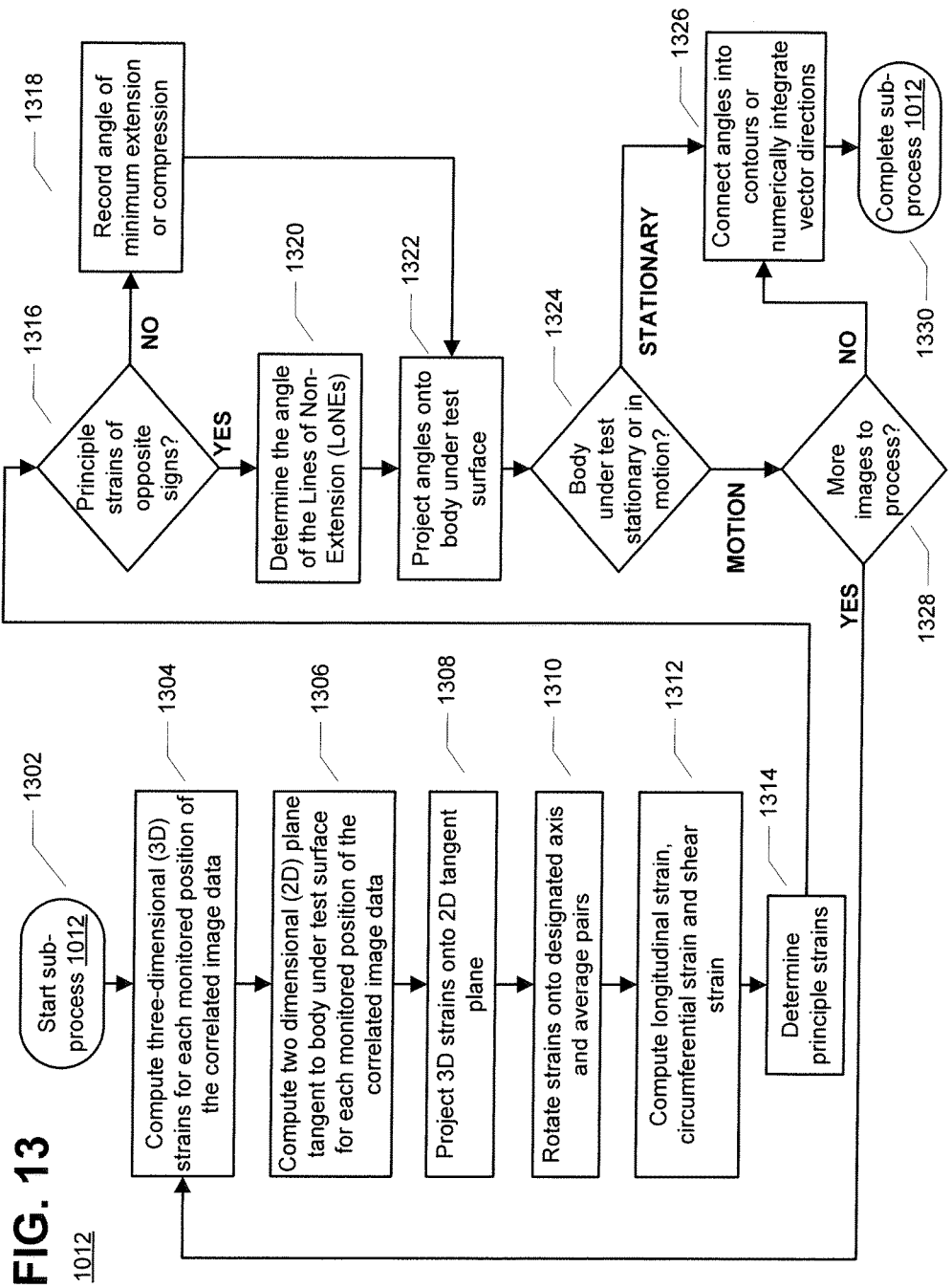
FIG. 13 is a flow diagram showing an illustrative process for determining strain and LoNEs in accordance with described embodiments.

FIG. 13 shows additional detail of block 1012 of FIG. 10. At block 1302, sub-process 1012 begins. At block 1304, 3D strain values are computed for each monitored point in the correlated images. In one embodiment, second order Green-Lagrange (or Lagrangian) strains c are determined by:

$$\varepsilon = \frac{l^2 - l_0^2}{2l_0^2} = \frac{\Delta l}{l_0} + \frac{(\Delta l)^2}{2l_0^2} \quad (13)$$

where l is the new distance between two points, $l_o$ is the original length between two points, and $\Delta l$ is the difference between the two. In other embodiments, the deformation gradient, F, is used to determined Green-Lagrange strains, E, determined by relationship (3) above, or Euler-Almansi strains, e, determined by relationship (4) above, where F is the deformation gradient given by relationship (2) above. F is the gradient of the mapping from the deformed frame to a reference frame, expressed by φ given by relationship (1) above. In some embodiments, both Green-Lagrange strains and Euler-Almansi strains are determined.

At block 1306, a two-dimensional (2D) plane tangent to the body skin at each monitored position is generated. In one embodiment, the two-dimensional (2D) plane is created by first averaging the normal vectors to the planes between each neighboring pair of strain vectors. This new "average" normal of, for example, eight (8) planes defines the normal vector to the tangential plane created at the monitored position. It should be appreciated that other techniques might also be used to compute this plane.

At block 1308, the 3D strains are projected onto the 2D tangent planes. As described, the directions of principal strain and non-extension are described as 2D vectors, such that the strain field can be determined with respect to a local 2D coordinate system on the surface of the object. The local coordinate system has the basis vectors $e_i'$ and the global coordinate system has the basis vectors $e_i$. The local coordinate system is defined with $e_3'$ aligned along the surface normal vector, $e_1'$ has no component along $e_2$ and is orthogonal to the surface normal, and $e_2'$ is the remaining orthogonal direction, $e_3' \times e_1'$.

At block 1310, the 3D strains are rotated onto the axes defined by the location of the monitored position and at block 1312, the rotated strains are averaged together to determine the longitudinal strain, the circumferential strain, and the shear strain. The vector fields can be rotated into the global reference frame. X' is the local 2D vector field to be rotated, X is the transformed global 3D vector field, and ($e_j \cdot e_i'$) represents the direction cosines. Thus, the rotation matrix R is given by:

$$X_i = (e_j \cdot e_i') X_j'$$

$$e_j \cdot e_i' = \cos \theta_{ji}$$

$$X = RX' \quad (15)$$

At this point, there are four vector fields in the global frame, the first and second principal strain directions and the first and second lines of non-extension directions.

At block 1314, the principal strains $E_1$ and $E_2$ are determined. In one embodiment, this is accomplished via eigenvector analysis as described above. At block 1316, if the principal strains $E_1$ and $E_2$ are of opposite signs, meaning there is both extension and compression, principal strains $E_1$ and $E_2$ are used to determine the angle of the LoNEs ($\phi$) in block 1320. In one embodiment, the LoNEs angles are given by:

$$\tan^2 \varphi = \frac{E_1(2+E_1)}{-E_2(2+E_2)} \quad (16a)$$

$$\tan^2 \varphi = \frac{(1-E_1)^2(E_1(2+E_1))}{(1+E_2)^2(1-(1+E_2)^2)} \quad (16b)$$

where (16a) is the angle between the primary eigenvector and the line of non-extension projected onto the initial position and (16b) is the same angle projected onto the deformed position. Sub-process 1012 proceeds to block 1322.

At block 1316, if the principal strains $E_1$ and $E_2$ are of the same sign, meaning there is only local extension or local compression, then the minimum extension or minimum compression is recorded, respectively, at block 1318.

Sub-process 1012 proceeds to block 1322. At block 1322, the determined LoNEs angles are projected onto the body surface (e.g., leg, knee, arm, elbow, etc.). At block 1324, if stationary analysis is being performed (e.g., only a single frame from the imaging system is being processed) sub-process 1012 proceeds to block 1326 where the angles are used to create non-extension vector directions that can be connected or numerically integrated to produce smooth continuous lines (e.g., contours). Sub-process 1012 completes at block 1330.

If, at block 1324 motion analysis is being performed (e.g., data collection system 504 produces multiple frames to capture motion of the body under test), then block 1328 implements a loop to repeat blocks 1304 through 1328 until all image frames are processed. Once all image frames are processed, at block 1330, sub-process continues to block 1326 where the angles are used to create non-extension vector directions that can be connected or numerically integrated to produce smooth continuous lines (e.g., contours). Sub-process 1012 completes at block 1330.

FIG. 14 shows additional detail of block 1016 of FIG. 10. At block 1402, sub-process 1016 begins. At block 1404, fabrics for various areas of a garment are selected based on fabric properties and the range of principal strain values mapped at locations of the body under test. For example, areas experiencing low magnitudes of strain could employ more rigid materials, while areas experiencing higher magnitudes of strain might employ more flexible materials. At block 1406, the fabrics are aligned based on the directionality of the determined strains. At block 1408, garment seams might be located in relation to the locations of determined LoNEs. It should be appreciated that placing seam lines along LoNEs is one of many ways the LoNEs might be used and that other seam placements might be employed. At block 1410, the overall garment is sized to a specific test subject, and at block 1412, a garment pattern and/or the garment are generated, for example by sizing and connecting the various fabrics. At block 1414, sub-process 1016 completes.

Figure 19:
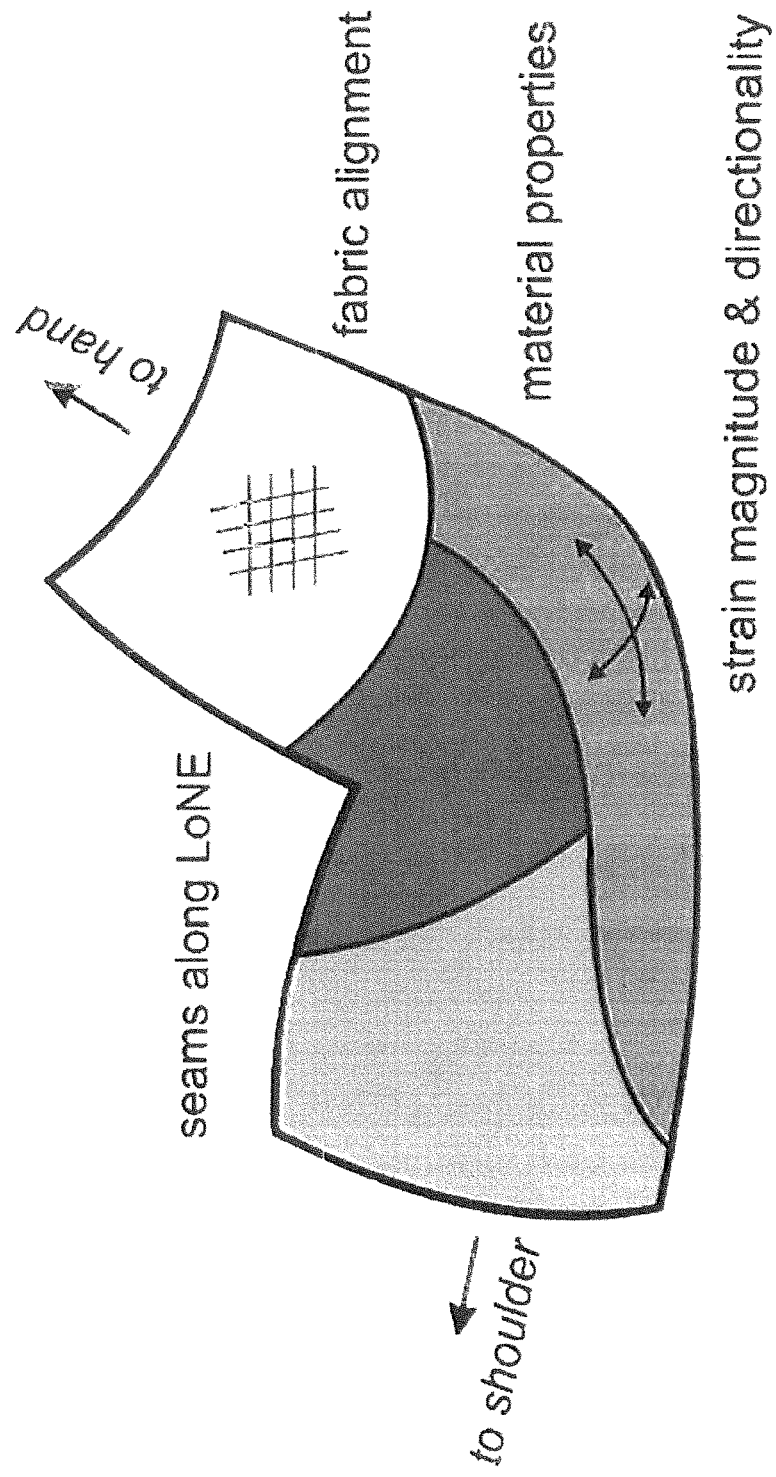
FIG. 19 is a diagram illustrating the application of LoNEs to garment design.

Referring to FIG. 19, it is shown how LoNEs maps can be employed to create garments and textile patterns for custom garments (e.g., skin tight garments) and other custom wearables for individual users. FIG. 19 shows a portion (e.g., an elbow) of a garment designed in accordance with described embodiments. For example, in addition to space suit design or other skin-tight garments, described embodiments might also be applied to the design of wearable technology systems that are placed on the body, exoskeletons, prosthetics, orthotics and other garments or systems that interface with skin. As shown in FIG. 19, a clothing designer might employ the skin strain information and the 3D visualizations to, for example, determine how to pattern the textile materials that will be used for a garment.

In order to make a tight fitting suit that is intimately interacting with the surface of the human body with large pressures, the suit should be synonymous with a second skin. The second skin should be similar to human skin that it will have a pre-tension that applies pressure and it should move with the body to not effect human motion. The designer and engineer can be informed by skin deformation visualizations. As shown in FIG. 19, various materials could be used to match the magnitude of deformation of human skin. Areas with larger deformations should have materials that are less stiff so as to not adversely affect mobility. The directionality of the strain field could be used to align and orient fabrics, seams or material properties. The LoNEs map could be used to determine how the fabric should be fused or sewn together.

For the particular case of space suits, mobility and energy expenditure are often the main design concerns. Although subjective metrics such as "comfort" and "fit" are not often highly considered in engineering applications, any space suit needs to emphasize these metrics, especially for an MCP suit that interacts closely with the skin. Matching the deformation of the suit with the deformation of the human body should reduce friction and increase comfort to provide a garment that is wearable for extended periods of time.

Figure 16:
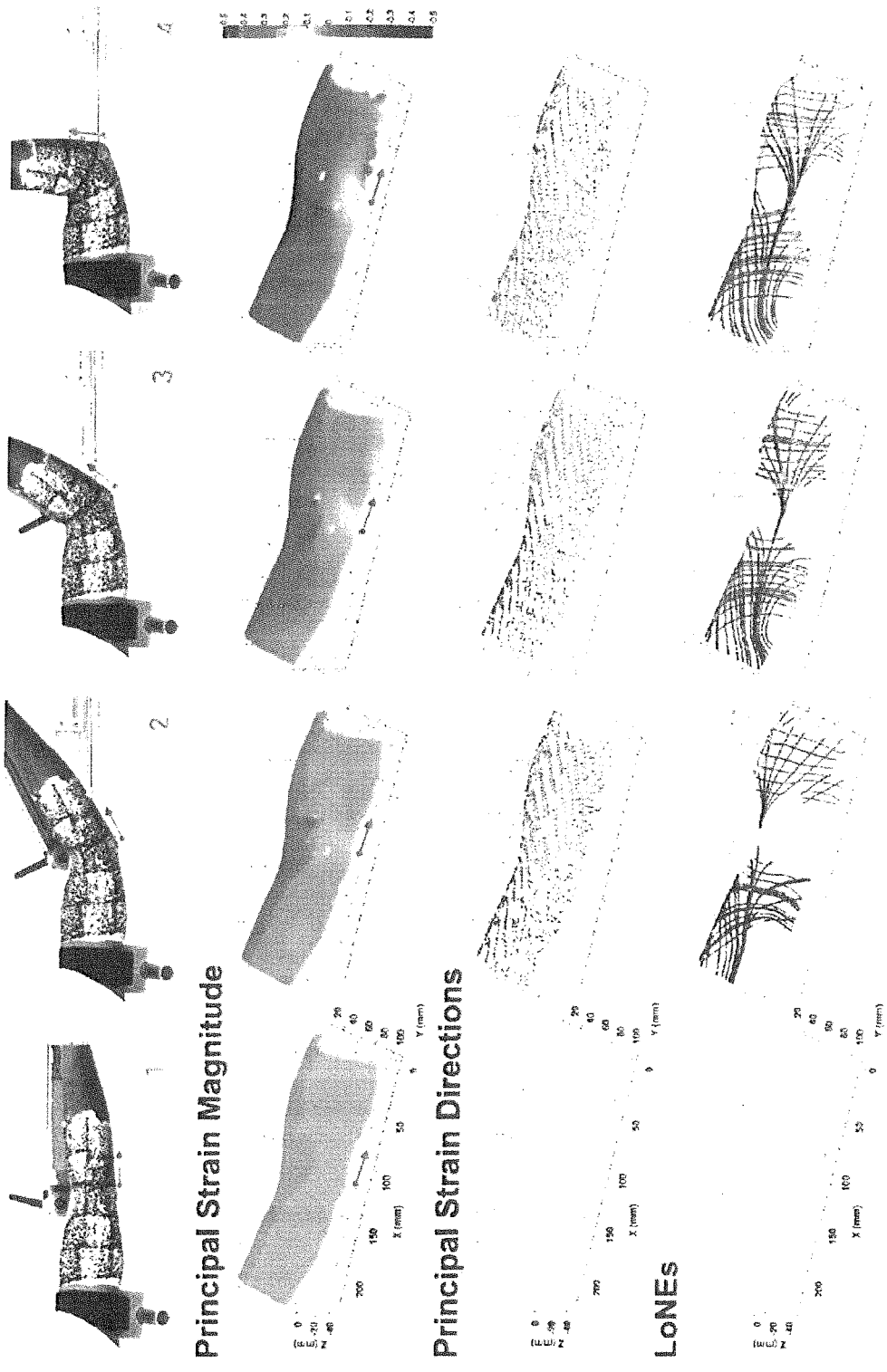
FIG. 16 is a diagram showing an illustrative relationship between captured images of a body under test, determined strain magnitudes and directions and LoNEs.

Referring back to FIG. 16, illustrative raw images captured by data collection system 504, images of principal strain magnitudes, principal strain directions and LoNEs determined by LoNEs processing system 508 are shown. As shown in FIG. 16, for described embodiments of system 500, the lateral side of a test subject's elbow joint has the unique texture or speckle pattern applied and images are captured quasi-statically as the subject poses at each position. LoNEs processing system 508 calculates the Green-Lagrangian strain tensor in a local coordinate system. The principal strain magnitudes, $E_1$ and $E_2$, determined. In a sample dataset, $E_1$ reaches 0.5 near the edge of the dataset and $E_2$ varies from −0.4 to 0.4, with both strain values approaching zero as moving away from the elbow joint. The posterior side of the elbow experiences tension in both principal directions. The anterior side of the elbow experiences compression in the longitudinal direction but tension in the circumferential direction. The directions of the principal strains are also shown. The streamline of the first direction of non-extension is as shown.

For example, FIG. 16 shows data for test subject A. The elbow joint angles are 0, 30, 60 and 90°, increasing from left to right. The data analysis is shown incrementally from top to bottom. The first row shows the raw images taken from one of cameras 602a-602d. The second row shows the magnitude of the second principal Green-Lagrange strain with the surface represented in the non-deformed configuration. The data shows that near the tip of the elbow the Green strain reaches 0.3. The third row shows the principal directions of the strain. The fourth row shows the LoNEs that were calculated for the direction of non-extension. The areas of the surface without LoNEs lines indicate areas that do not have LoNE directions (e.g., areas where principal strains $E_1$ and $E_2$ have the same sign). Principal directions can also be visualized as lines using the same methodology that was applied to the directions of non-extension. These lines are referred to as the lines of principal strain.

Figure 17:
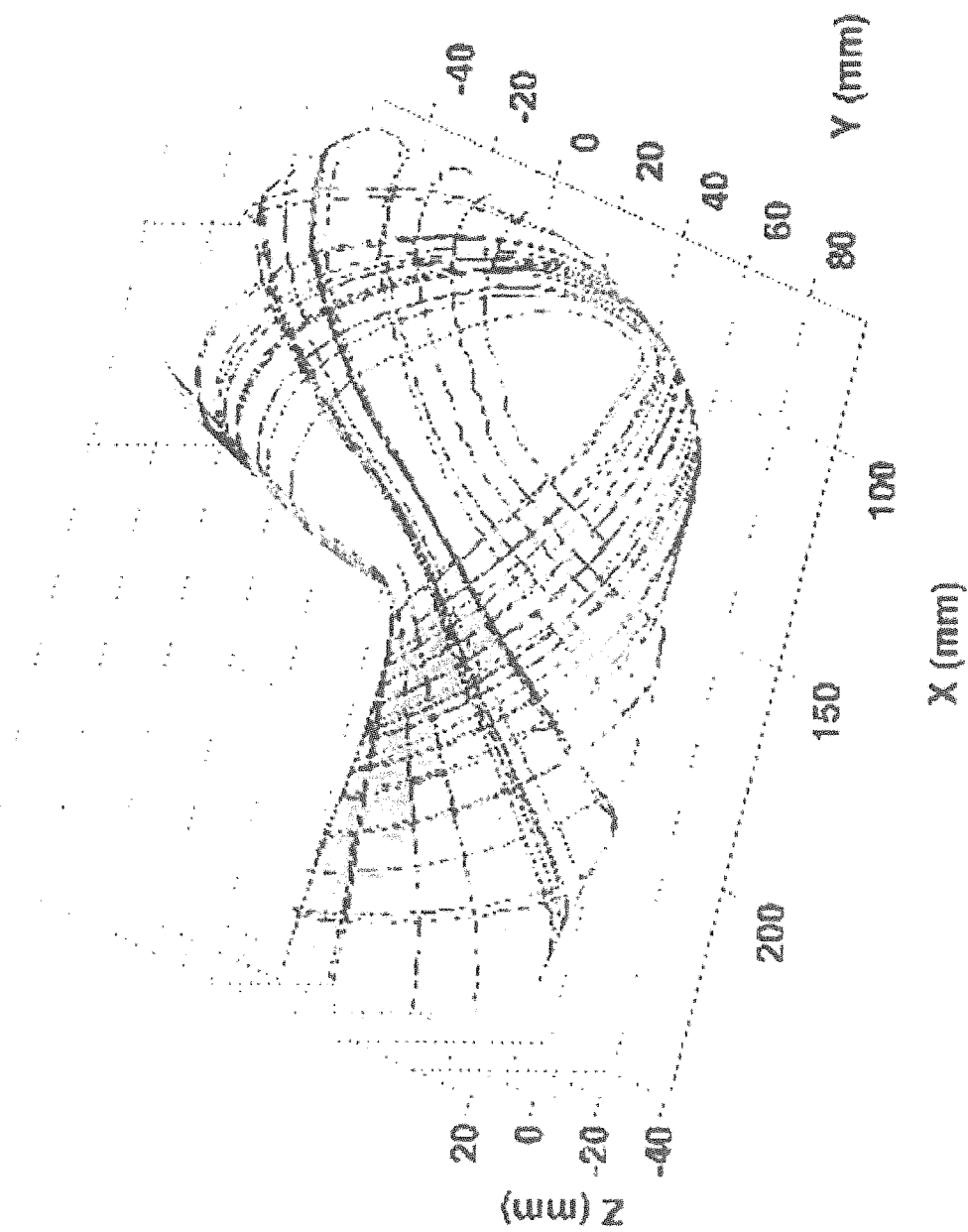
FIG. 17 is a diagram illustrating lines of principal strain projected onto a deformed configuration at 90° elbow flexion.

FIG. 17 shows the LoNEs and the lines of principal strain projected onto the deformed configuration at 90° elbow flexion. The lines of principal strain were calculated using the strain field at 90° elbow flexion using a uniform strain field where the magnitude of each principal direction is unity. This is to visualize the general directionality of the field. In traditional fluids, the magnitude of each vector would be taken into account for the streamline calculation. For test subject A, principal strains $E_1$ and $E_2$ near the olecranon approach 0.5 and 0.3 respectively. $E_2$ approaches a minimum of −0.4 within the cubital fossa.

As described herein, LoNEs are assumed to remain at a consistent length throughout deformation. To check this assumption, the LoNEs calculated at 90° elbow flexion were projected to all other deformations. The Euclidean arc length was calculated for each LoNE at each deformation. For comparison, the same process was carried out for the lines of principal strain. The sample size was 54 LoNEs and 46 lines of principal strain, where 8 lines of principal strain were not considered because they could not be successfully projected. The LoNEs remain with 6% of their original length at 0° elbow flexion whereas lines along the principal directions changed 17%. Indeed LoNEs change length when examined throughout the deformation, but these lines undergo a minimum amount of extension when compared to other lines that could be drawn on the surface.

The strain field for subjects A through F was measured. The range of principal strain is reported in Table 3, which shows the large range of strain experienced by human skin.

TABLE 3

| Subject | A | B | C | D | E | F |
|---------|---|---|---|---|---|---|
| $E_i$ (min) | −0.41 | −0.43 | −0.34 | −0.44 | −0.42 | −0.49 |
| $E_i$ (max) | 0.46 | 0.36 | 0.49 | 0.60 | 0.42 | 0.46 |

Figure 18:
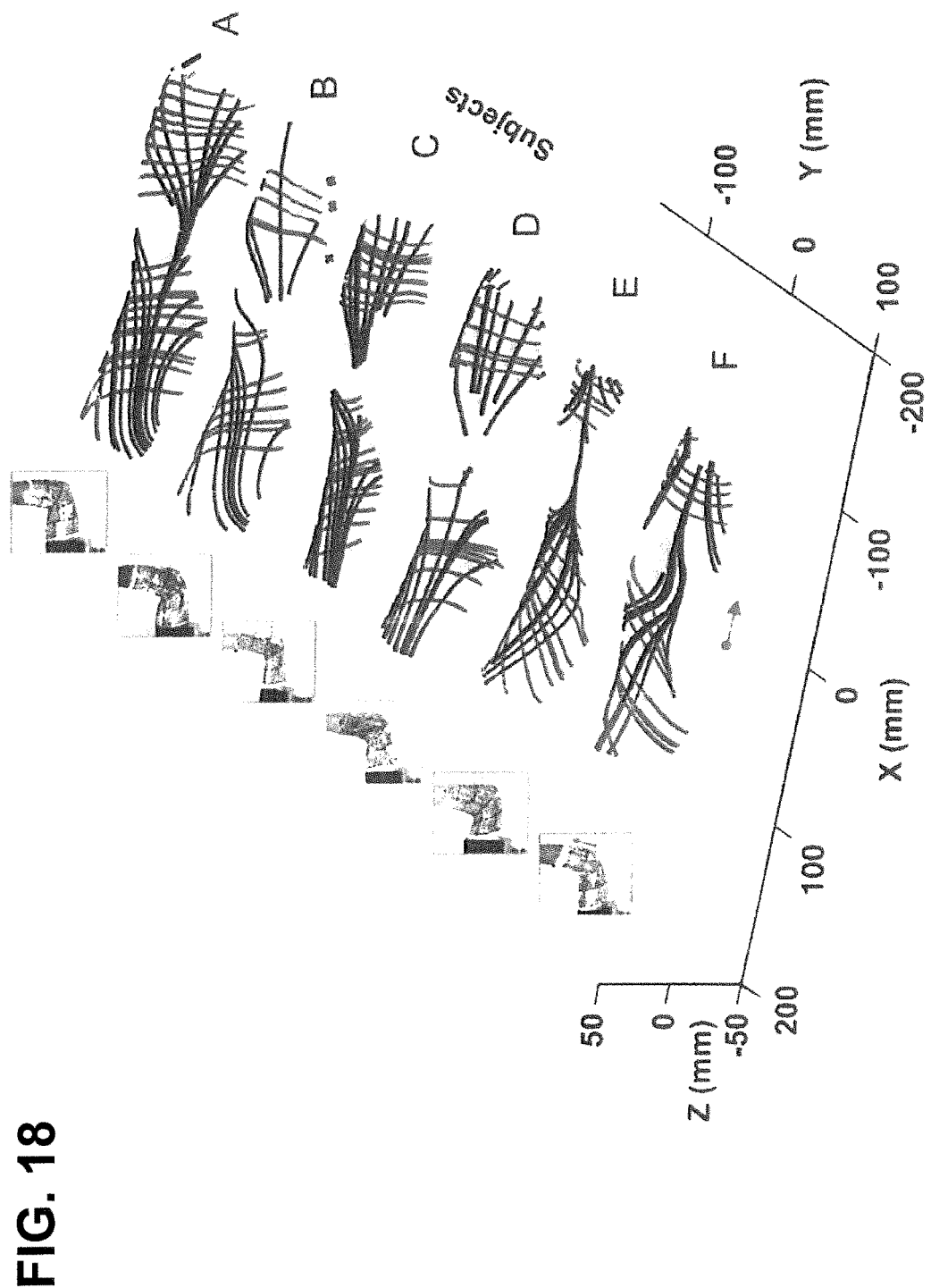
FIG. 18 is a diagram illustrating the calculated LoNEs of six test subjects with the elbow joint at 90° and similar seed point locations.

The LoNEs for test subjects A-F are shown in FIG. 18. The LoNEs were calculated when the elbow joint was at 90° for each subject using similar locations for the seed points. The LoNEs are shown in the undeformed configuration.

The strain field was measured near 1 mm² resolution using 3D DIC and the LoNEs were calculated as continuous streamlines using seed points. As shown in FIG. 18, despite varying subject anthropometrics, the LoNEs maps look similar between subjects. Further, FIG. 18 shows that one set of LoNEs consistently converge along the brachioradialis muscle. Thus, described embodiments might, for example during sub-process 1014, predict the LoNE map of an individual test subject in order to develop custom garments.

Thus, described embodiments measure human skin strain using 3D DIC at a spatial resolution on the order of 1 mm². The millimeter scale mesh size is achieved by how DIC computes the displacements where images are broken down into small subsets of pixels. Subsets overlap, increasing resolution beyond dividing the image by subset size. The streamline approach is a continuous approach that is less affected by data resolution, mesh type, or mesh connectivity than other connection methods. The streamline ending location becomes more variable the further the vector field is integrated away from the seed point, so seed point selection is done to maintain short streamline segments.

Reference herein to "one embodiment" or "an embodiment" means that a particular feature, structure, or characteristic described in connection with the embodiment can be included in at least one embodiment of the claimed subject matter. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the words "exemplary" and "illustrative" are used herein to mean serving as an example, instance, or illustration. Any aspect or design described herein as "exemplary" or "illustrative" is not necessarily to be construed as preferred or advantageous over other aspects or designs. Rather, use of the words "exemplary" and "illustrative" is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

To the extent directional terms are used in the specification and claims (e.g., upper, lower, parallel, perpendicular, etc.), these terms are merely intended to assist in describing the embodiments and are not intended to limit the claims in any way. Such terms, do not require exactness (e.g., exact perpendicularity or exact parallelism, etc.), but instead it is intended that normal tolerances and ranges apply. Similarly, unless explicitly stated otherwise, each numerical value and range should be interpreted as being approximate as if the word "about", "substantially" or "approximately" preceded the value of the value or range.

Some embodiments might be implemented in the form of methods and apparatuses for practicing those methods. Further, as would be apparent to one skilled in the art, various functions of circuit elements might also be implemented as processing blocks in a software program. Described embodiments might also be implemented in the form of program code embodied in tangible media, such as magnetic recording media, hard drives, floppy diskettes, magnetic tape media, optical recording media, compact discs (CDs), digital versatile discs (DVDs), solid state memory, hybrid magnetic and solid state memory, or any other machine-readable storage medium, wherein, when the program code is loaded into and executed by a machine, such as a computer, the machine becomes an apparatus for practicing the claimed invention. Described embodiments might also be implemented in the form of program code, for example, whether stored in a storage medium, loaded into and/or executed by a machine, or transmitted over some transmission medium or carrier, such as over electrical wiring or cabling, through fiber optics, or via electromagnetic radiation, wherein, when the program code is loaded into and executed by a machine, such as a computer, the machine becomes an apparatus for practicing the claimed invention. When implemented on a processing device, the program code segments combine with the processor to provide a unique device that operates analogously to specific logic circuits. Such processing devices might include, for example, a general purpose microprocessor, a digital signal processor (DSP), a reduced instruction set computer (RISC), a complex instruction set computer (CISC), an application specific integrated circuit (ASIC), a field programmable gate array (FPGA), a programmable logic array (PLA), a microcontroller, an embedded controller, a multi-core processor, and/or others, including combinations of the above. Described embodiments might also be implemented in the form of a bitstream or other sequence of signal values electrically or optically transmitted through a medium, stored magnetic-field variations in a magnetic recording medium, etc., generated using a method and/or an apparatus as recited in the claims.

Also for purposes of this description, the terms "couple," "coupling," "coupled," "connect," "connecting," or "connected" refer to any manner known in the art or later developed in which energy is allowed to be transferred between two or more elements, and the interposition of one or more additional elements is contemplated, although not required. Conversely, the terms "directly coupled," "directly connected," etc., imply the absence of such additional elements. Signals and corresponding nodes or ports may be referred to by the same name and are interchangeable for purposes here.

As used herein in reference to an element and a standard, the term "compatible" means that the element communicates with other elements in a manner wholly or partially specified by the standard, and would be recognized by other elements as sufficiently capable of communicating with the other elements in the manner specified by the standard. The compatible element does not need to operate internally in a manner specified by the standard.

It should be understood that the steps of the methods set forth herein are not necessarily required to be performed in the order described, and the order of the steps of such methods should be understood to be merely illustrative. Likewise, additional steps may be included in such methods, and certain steps may be omitted or combined, in methods consistent with various embodiments.

It will be further understood that various changes in the details, materials, and arrangements of the parts that have been described and illustrated herein might be made by those skilled in the art without departing from the scope of the following claims.

We claim:

1. A method for use in a system for measuring surface deformation and strain of a surface of a test object, the method comprising:
   acquiring, by an imaging device, images of the surface, the surface having a surface pattern;
   grouping the images into one or more image sets;
   performing three dimensional image correlation on each of the image sets to determine deformation and strain data;
   stitching the deformation and strain data from the image sets into one dataset;
   determining, by at least one processor, principal strains and lines of non-extension (LoNEs) directions;
   determining, by the at least one processor, one or more LoNEs streamlines;
   determining, by the at least one processor, lines of maximum and minimum extensions;
   based on one or more of the determined principal strains, the LoNEs directions, the one or more LoNEs streamlines and the lines of maximum and minimum extensions, generating a pattern for one or more customized coverings for the test object; and
   based on the generated pattern, generating the one or more customized coverings.

2. The method of claim 1, further comprising:
   generating visualizations for the principal strains, LoNE streamlines, maximum and minimum extension streamlines in three dimensions, the visualizations being generated for presentation on a rendering device.

3. The method of claim 2, wherein the surface is human skin and the test object is a human, and wherein the one or more customized coverings comprise at least one of: custom garments, custom orthotics, custom prosthetics and custom wearable electronic devices.

4. The method of claim 1, further comprising:
   generating the surface pattern, the surface pattern having a pattern with a granularity determined to provide image tracking resolution of approximately 1 mm$^2$; and
   applying the generated surface patter to the surface.

5. The method of claim 4, further comprising:
   generating an application tool to apply the surface pattern to the surface.

6. The method of claim 1, wherein stitching the deformation and strain data from the image sets into one dataset comprises:
   converting the image sets from into a plurality of meshes; and
   stitching the meshes together at points of overlap between each mesh.

7. The method of claim 6, further comprising:
   at a point of overlap between the meshes, merging data of the image sets by re-meshing the data of the image sets at the overlap point.

8. The method of claim 6, further comprising:
   at a point of overlap between the meshes, averaging data of the image sets at the overlap point.

9. The method of claim 6, further comprising:
   at a point of overlap between the meshes:
      determining a measurement quality index, q, and keeping data from the image sets that reach a predetermined threshold of q, and discarding data from the image sets that do not reach the predetermined threshold.

10. The method of claim 9, wherein q is defined as an inverse of a standard deviation of a matching error of the image sets given by $q=1/\sigma$.

11. The method of claim 6, wherein the image sets are in a curvilinear grid data format, and wherein the meshes are triangular meshes.

12. The method of claim 1, wherein determining principal strains and lines of non-extension (LoNEs) directions comprises:
   identifying and determining motion of, based on the surface pattern, pixel groups from an image of an initial position of the surface and from an image of a deformed position of the surface;

determining one or more strains of each pixel group;
projecting the determined strains onto a two-dimensional (2D) plane tangent to the surface;
rotating the projected strains onto axes defined with respect to the surface;
based on the rotated strains, generating a longitudinal strain, a circumferential strain, a shear strain and principal strains for each pixel group;
if the principal strains associated with each pixel group have opposite signs, determining an angle of a line of non-extension for the pixel group based on the principal strains;
if the principal strains associated with each pixel group have opposite signs, determining an angle of minimum extension or minimum compression for the pixel group;
projecting the determined angle of a line of non-extension or angles of minimum extension or minimum compression for each pixel group onto the surface; and
connecting angles of lines of non-extension into streamlines.

13. The method of claim 12 wherein determining one or more strains surrounding each marker point comprises calculating at least one of: Lagrangian strains and Euler-Almansi strains.

14. The method of claim 12, further comprising:
generating a 2D tangential plane by averaging normal vectors to the planes between neighboring pairs of strain vectors associated with a corresponding pixel group, wherein a neighboring pair of strain vectors comprises strain vectors associated with pixel groups that are adjacent to one another.

15. The method of claim 1, wherein determining one or more LoNEs streamlines and determining lines of maximum and minimum extensions comprises:
selecting one or more seed points within the image sets;
linearly interpolating a vector filed of LoNEs directions of the image sets by transforming to a local tangential coordinate system;
determining streamlines where a current position plus a velocity at that point multiplied by a time step equals a new position; and
translating the determined streamlines from a 2D coordinate system to a 3D coordinate system.

16. The method of claim 1, wherein the images are acquired by one or more stereoscopic camera pairs.

17. The method of claim 1, wherein the imaging device includes at least one of: one or more optical cameras, computed tomography (CT) and magnetic resonance imaging (MRI).

18. The method of claim 1, further comprising:
acquiring deformation data from one or more sensors in contact with the surface.

19. A system for measuring surface deformation and strain using digital image correlation of a surface of a test object, the system comprising:
a memory;
a data collection system configured to acquire images of the surface, the surface having a surface pattern; and
at least one processor operatively coupled to the memory and the data collection system, the at least one processor being configured to:
group the images into one or more image sets;
perform three dimensional image correlation on each of the image sets to determine deformation and strain data;
stitch the deformation and strain data from the image sets into one dataset;
determine principal strains and lines of non-extension (LoNEs) directions;
determine one or more LoNEs streamlines;
determine lines of maximum and minimum extensions;
generate, based on one or more of the determined principal strains, the LoNEs directions, the one or more lines of non-extension (LoNEs) streamlines and the lines of maximum and minimum extensions, a pattern for one or more customized coverings for the test object; and
generate, based on the pattern, the one or more customized coverings.

20. The system of claim 19, wherein the surface is human skin and the test object is a human, and wherein the one or more custom coverings comprise at least one of: custom garments, custom orthotics, custom prosthetics and custom wearable electronic devices.

21. The system of claim 19, wherein the data collection system comprises one or more stereoscopic camera pairs.

22. The system of claim 19, wherein the data collection system comprises at least one of: one or more optical cameras, computed tomography (CT) imager, and a magnetic resonance imager (MRI).

23. The system of claim 19, wherein the data collection system comprises one or more sensors in contact with the surface.

24. A non-transitory machine-readable storage medium, having encoded thereon program code, wherein, when the program code is executed by a machine, the machine implements a method for measuring surface deformation and strain using digital image correlation of a surface of a test object, the method comprising:
acquiring images of the surface, the surface having a surface pattern;
grouping the images into one or more image sets;
performing three dimensional image correlation on each of the image sets to determine deformation and strain data;
stitching the deformation and strain data from the image sets into one dataset;
determining principal strains and lines of non-extension (LoNEs) directions;
determining one or more LoNEs streamlines;
determining lines of maximum and minimum extensions;
based on one or more of the determined principal strains, the LoNEs directions, the one or more LoNEs streamlines and the lines of maximum and minimum extensions, generating a pattern for one or more customized coverings for the test object; and
based on the generated pattern, generating the one or more customized coverings.

25. The non-transitory machine-readable storage medium of claim 24, wherein the surface is human skin and the test object is a human, and wherein the one or more custom coverings comprise at least one of: custom garments, custom orthotics, custom prosthetics and custom wearable electronic devices.

* * * * *